(12) United States Patent
Kumar et al.

(10) Patent No.: US 12,036,515 B2
(45) Date of Patent: Jul. 16, 2024

(54) THIN-FILM COMPOSITE MEMBRANE AND METHODS OF MAKING AND USING THE SAME

(71) Applicant: THE PENN STATE RESEARCH FOUNDATION, University Park, PA (US)

(72) Inventors: Manish Kumar, Austin, TX (US); Woochul Song, State College, PA (US); Yue-xiao Shen, El Cerrito, CA (US); Chao Lang, State College, PA (US)

(73) Assignee: THE PENN STATE RESEARCH FOUNDATION, University Park (PA)

( * ) Notice: Subject to any disclaimer, the term of this patent is extended or adjusted under 35 U.S.C. 154(b) by 518 days.

(21) Appl. No.: 17/282,082

(22) PCT Filed: Oct. 2, 2019

(86) PCT No.: PCT/US2019/054224
§ 371 (c)(1),
(2) Date: Apr. 1, 2021

(87) PCT Pub. No.: WO2020/072594
PCT Pub. Date: Apr. 9, 2020

(65) Prior Publication Data
US 2021/0370240 A1 Dec. 2, 2021

Related U.S. Application Data

(60) Provisional application No. 62/739,912, filed on Oct. 2, 2018.

(51) Int. Cl.
*B01D 69/12* (2006.01)
*B01D 53/22* (2006.01)
*B01D 67/00* (2006.01)
*B01D 69/02* (2006.01)
*B01D 69/10* (2006.01)
*B01D 71/56* (2006.01)
*B01D 71/60* (2006.01)
*B01D 71/64* (2006.01)
*B01D 71/68* (2006.01)
*C07C 7/144* (2006.01)

(52) U.S. Cl.
CPC ........ *B01D 69/125* (2013.01); *B01D 53/228* (2013.01); *B01D 67/0006* (2013.01); *B01D 69/02* (2013.01); *B01D 69/105* (2013.01); *B01D 71/56* (2013.01); *B01D 71/60* (2013.01); *B01D 71/64* (2013.01); *B01D 71/68* (2013.01); *C07C 7/144* (2013.01); *B01D 2325/02* (2013.01); *B01D 2325/04* (2013.01)

(58) Field of Classification Search
None
See application file for complete search history.

(56) References Cited

U.S. PATENT DOCUMENTS

2009/0114596 A1* 5/2009 Kriesel ............... C07D 259/00
95/45
2015/0273389 A1* 10/2015 Liu ...................... C08G 18/48
95/45

* cited by examiner

*Primary Examiner* — Tam M Nguyen
(74) *Attorney, Agent, or Firm* — McKee, Voorhees & Sease, PLC

(57) ABSTRACT

The present invention relates to a thin-film composite (TFC) membrane composition comprising macrocycles. The invention also relates in part to a method of fabricating a TFC membrane and to a method of using the TFC membrane to separate a desired liquid or gas from a liquid or gas mixture.

5 Claims, 14 Drawing Sheets i-butane : iso-butane
i-butene : iso-butene

THIN-FILM COMPOSITE MEMBRANE AND METHODS OF MAKING AND USING THE SAME

CROSS-REFERENCE TO RELATED APPLICATIONS

This application is a U.S. national phase application filed under 35 U.S.C. § 371 claiming benefit to International Patent Application No. PCT/US2019/054224, filed Oct. 2, 2019, which is entitled to priority under 35 U.S.C. § 119(e) to U.S. Provisional Application No. 62/739,912, filed on Oct. 2, 2018, each of which applications is hereby incorporated herein by reference in its entirety.

STATEMENT OF FEDERALLY SPONSORED RESEARCH OR DEVELOPMENT

This invention was made with government support under Grant No. CBET1552571 awarded by the National Science Foundation. The Government has certain rights in the invention.

BACKGROUND OF THE INVENTION

Membranes act as selective barriers which allow certain chemical species to pass while retaining others and therefore are useful in a wide variety of separation processes including reverse osmosis, dialysis, electrodialysis, ultrafiltration, nanofiltration, and gas separations. Thin-film composite (TFC) membranes are a type of semipermeable membrane commonly used in water purification and water desalination systems. Considerable research and development has been performed with the goal of making very thin and highly selective TFC membranes. Despite research into these membranes, it is difficult to design the molecular selectivity of current TFC membranes due to the unknown properties of TFC membrane materials such as free voids structures and intrinsic microporosities.

TFC membranes typically comprise a polymeric matrix with a non-uniform pore distribution. Pore size, shape, and distribution can vary in the non-uniform matrix element, which results in low selectivity of the solutes retained, or low permeability of the solvent. This selectivity/permeability tradeoff is a major constraint on the performance of TFC membranes for applications such as gas and hydrocarbon separations, water desalination, water filtration, kidney dialysis, and pharmaceutical separations. Overcoming the selectivity/permeability tradeoff requires membranes with uniform pore sizes, shapes, and distribution that could be achieved through separation of the matrix and pore elements.

Thus, there is a need in the art for TFC membranes with enhanced solvent permeability and controllable molecular selectivity. The present invention addresses this unmet need in the art.

SUMMARY OF THE INVENTION

In one aspect, the present invention relates to a thin film composite (TFC) membrane comprising a porous layer of at least one organic polymer, wherein the organic polymer further comprises macrocycles. In one embodiment, the TFC membrane comprises a macrocycle selected from the group consisting of: pillar[4]arene, pillar[5]arene, pillar[6]arene, pillar[7]arene, pillar[8]arene, crown-ether, calixarenes, porphyrins, cyclodextrins, and combinations thereof. In one embodiment, the TFC membrane further comprises a polymeric support. In one embodiment, the macrocycles in the TFC membrane comprise a pore having a diameter of 1 to 10 Å. In one embodiment, the TFC membrane has a thickness between 1 nm and 1000 nm.

In another aspect, the present invention also relates to a method of making a TFC membrane, the method comprising: providing a solution comprising a first organic species, providing a macrocycle, mixing the solution comprising the organic species and the macrocycle to form a mixture, and forming a TFC membrane. In one embodiment, the step of mixing the solution comprising the first organic species and the macrocycle further comprises the step of mixing a second organic species. In one embodiment, the step of forming a TFC membrane comprises polymerizing the mixture. In one embodiment, the step of providing a solution comprising a first organic species comprises providing a solution of water and a solvent selected from the group consisting of methanol, ethanol, isopropanol, 1-propanol, n-butanol, sec-butanol, isobutanol, and tert-butanol. In one embodiment, the step of providing a macrocycle further comprises the step of providing a support. In one embodiment, the step of providing a support further comprises the step of irradiating the support with a UV light in an atmosphere of ozone. In one embodiment, the step of forming a TFC membrane comprises the step of forming a TFC membrane on a support.

In another aspect, the present invention also relates to a method of separating a first species from a mixture of the first species and a second species, the method comprising: providing a TFC membrane comprising a porous layer of at least one organic polymer, wherein the porous layer further comprises macrocycles; applying the mixture to a feed side of the TFC membrane; causing the first species to pass through the TFC membrane; and collecting the first species from an opposite side of the TFC membrane or the second species from the feed side of the TFC membrane. In one embodiment, the step of causing the first mixture to pass through the TFC membrane further comprises the step of applying a pressure of −1 bar to 500 bar. In one embodiment, the mixture comprises a linear $C_4$ hydrocarbon and a branched $C_4$ hydrocarbon and the first species comprises the linear $C_4$ hydrocarbon.

BRIEF DESCRIPTION OF THE DRAWINGS

The following detailed description of preferred embodiments of the invention will be better understood when read in conjunction with the appended drawings. It should be understood that the invention is not limited to the precise arrangements and instrumentalities of the embodiments shown in the drawings.

FIG. 10, comprising FIG. 10A depicts methanol (MeOH) permeances. FIG. 10B depicts organic dye rejection profiles. The data show that P[5] macrocycle TFC membranes can be activated by isopropanol (IPA) and polyamide membranes can be activated by dimethylformamide (DMF), respectively.

DETAILED DESCRIPTION

Figure 1:
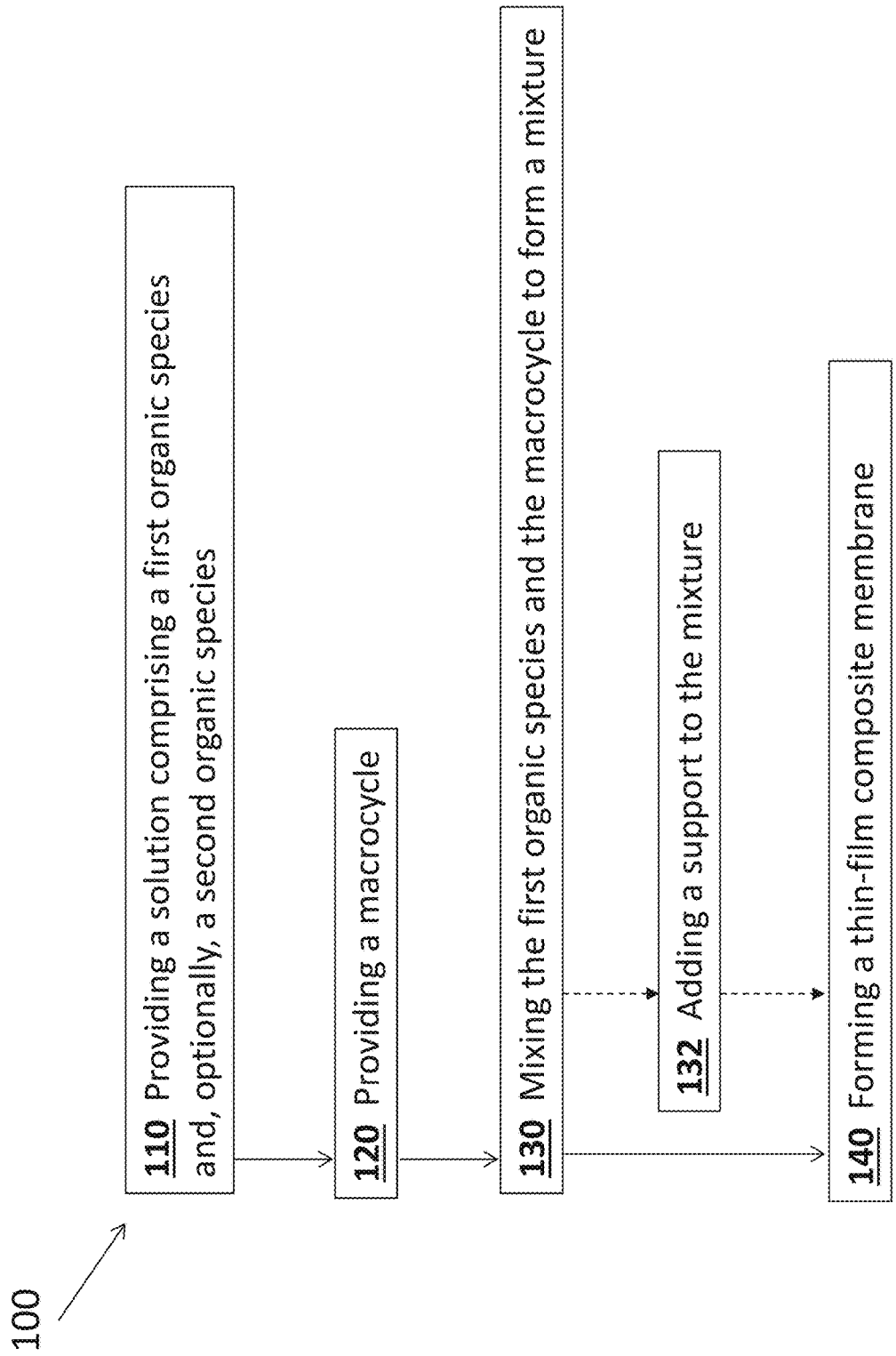
FIG. 1 is a flowchart of an exemplary method for making a thin-film composite (TFC) membrane.
Figure 2:
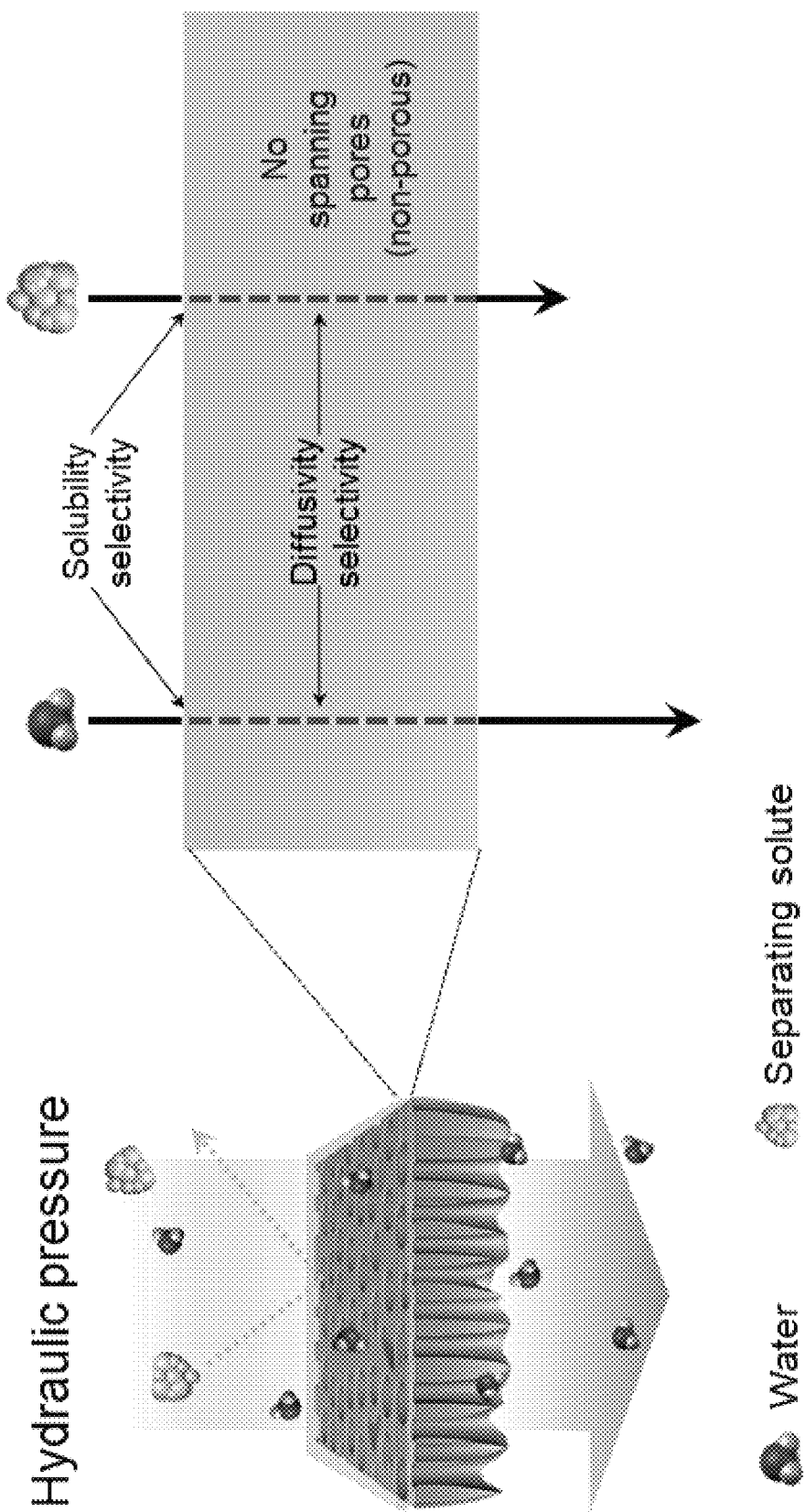
FIG. 2 depicts a schematic illustration of conventional TFC membrane architecture (left). Current TFC membranes are considered to be non-porous membranes with hard to control free void distribution (right).
Figure 3:
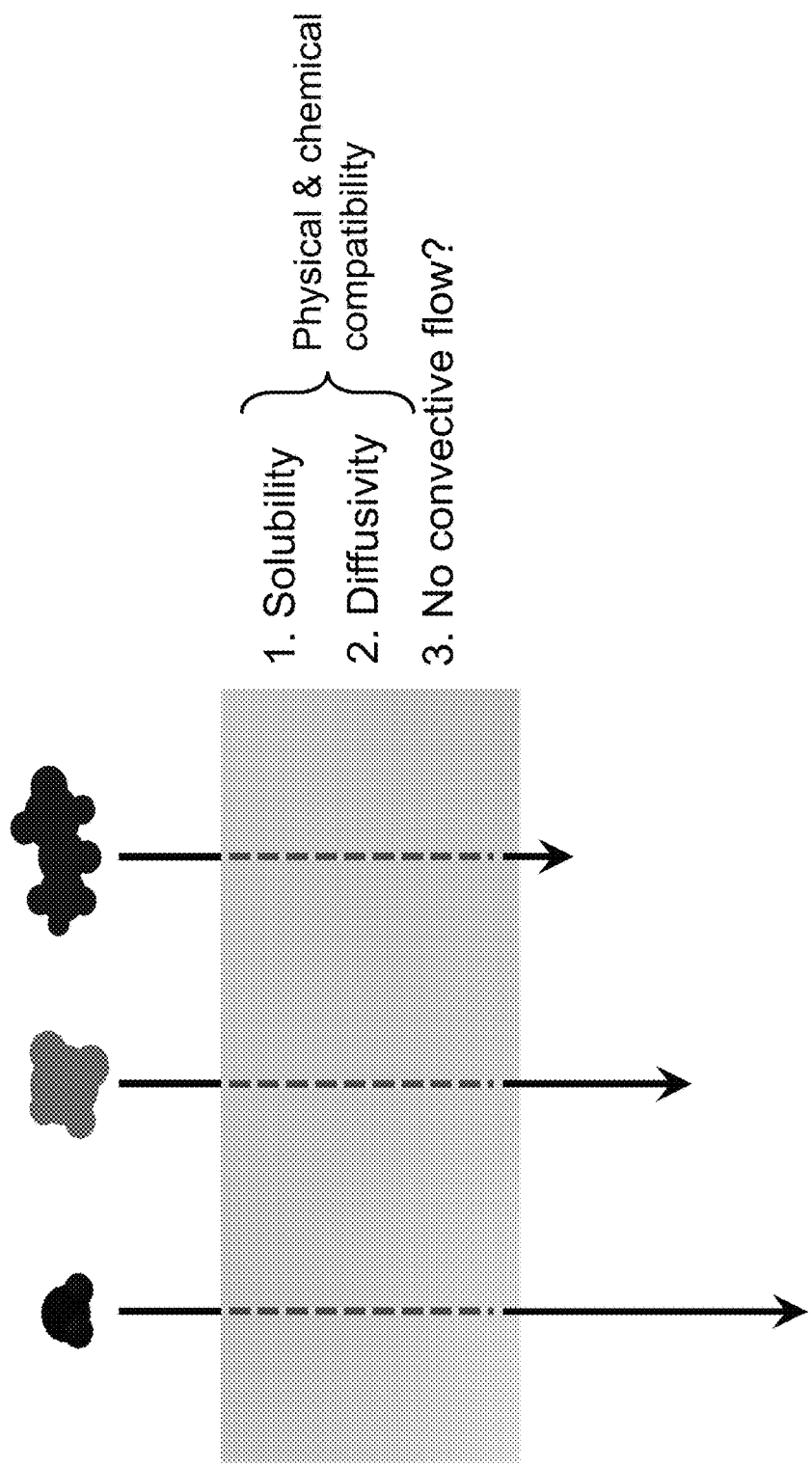
FIG. 3 depicts a schematic demonstrating that current TFC membranes are practically impossible to design selectivity at angstrom scale.
Figure 4:
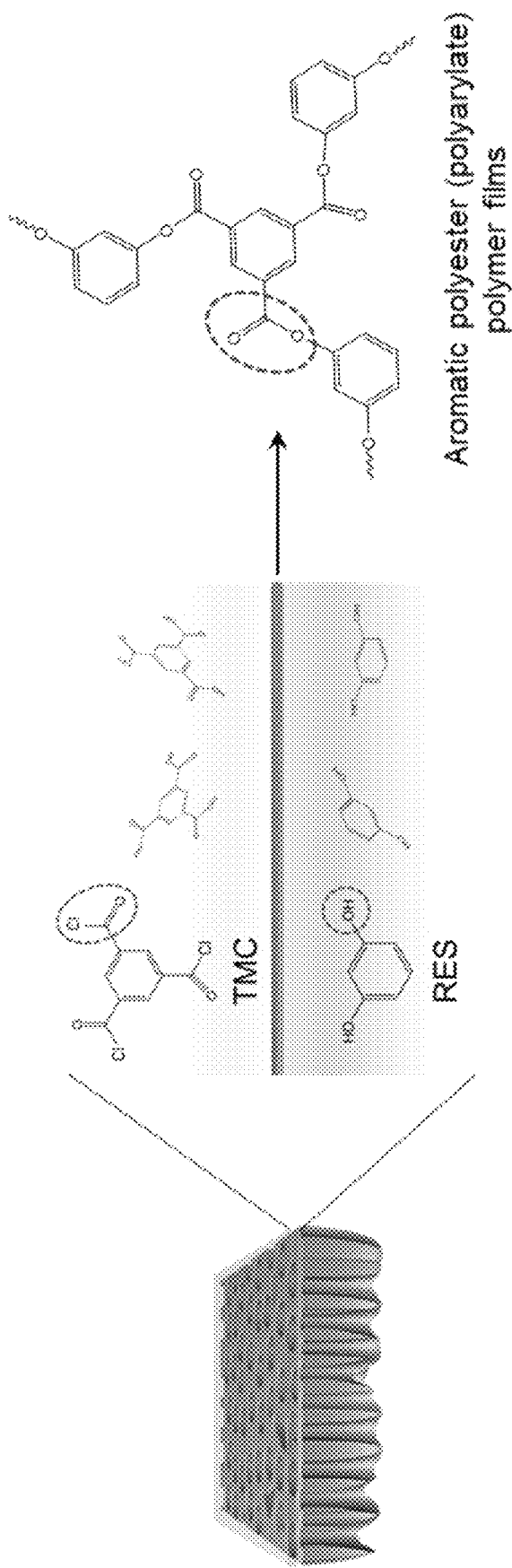
FIG. 4 depicts traditional TFC membranes made by interfacial polymerization (IP) wherein RES refers to 1,3-benzenediol (i.e. resorcinol) and TMC refers to 1,3,5-benzenetricarbonyltrichloride (i.e. trimesoyl chloride).
Figure 5:
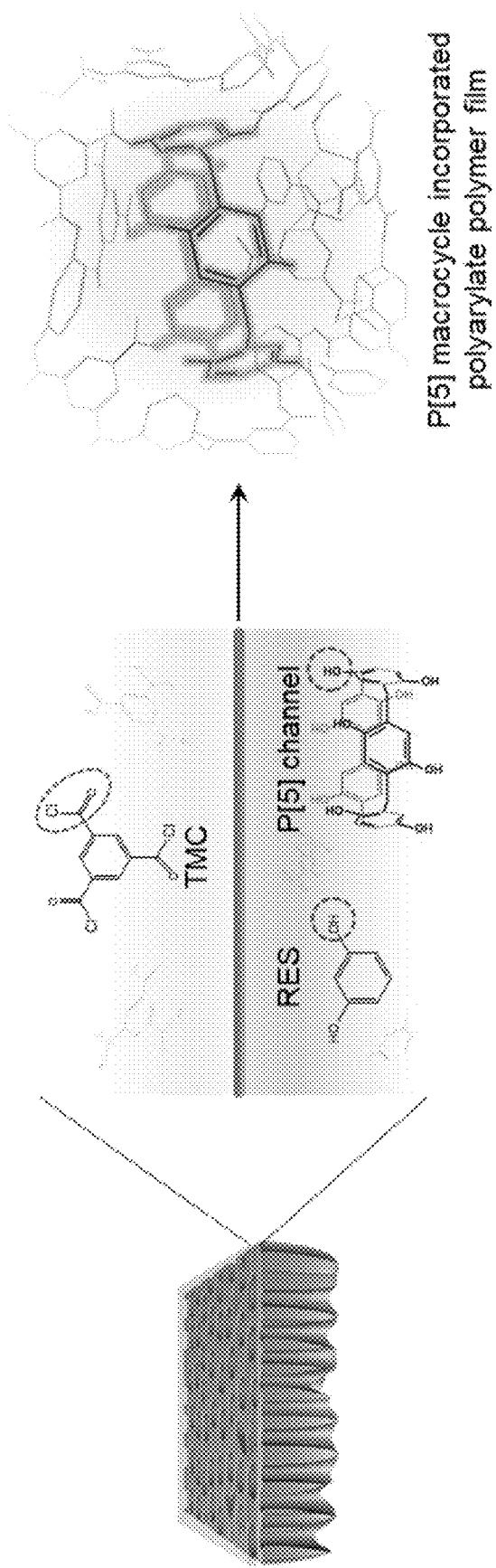
FIG. 5 depicts a schematic demonstrating a P[5] (pillar [5]arene) macrocycle incorporation into a TFC membrane via IP. Macrocycle TFC membranes can be prepared via conventional IP method by simply adding macrocycles into first monomer solution at membrane fabrication step. Incorporated macrocycles provide unitary free volume elements inside the polymer which result in high selectivity at angstrom scale separation.
Figure 6:
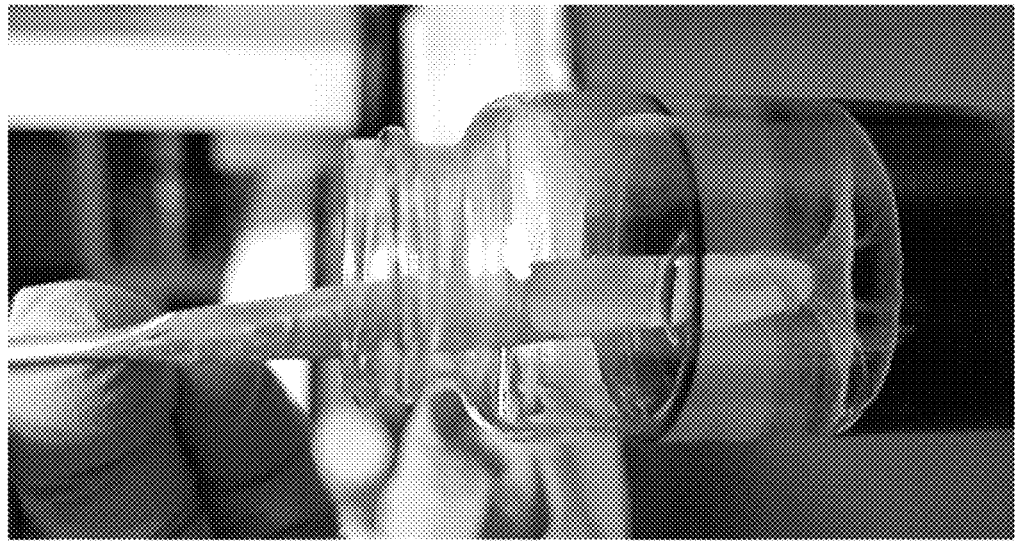
FIG. 6 depicts a polyarylate polymer film formed from pillar[5]arene, RES, and TMC.
Figure 6:
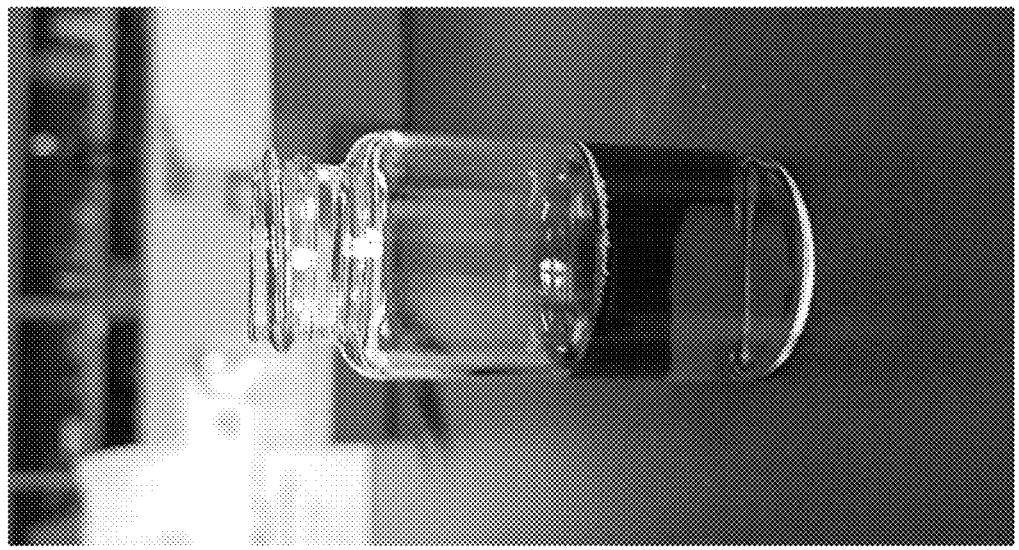
Figure 7:
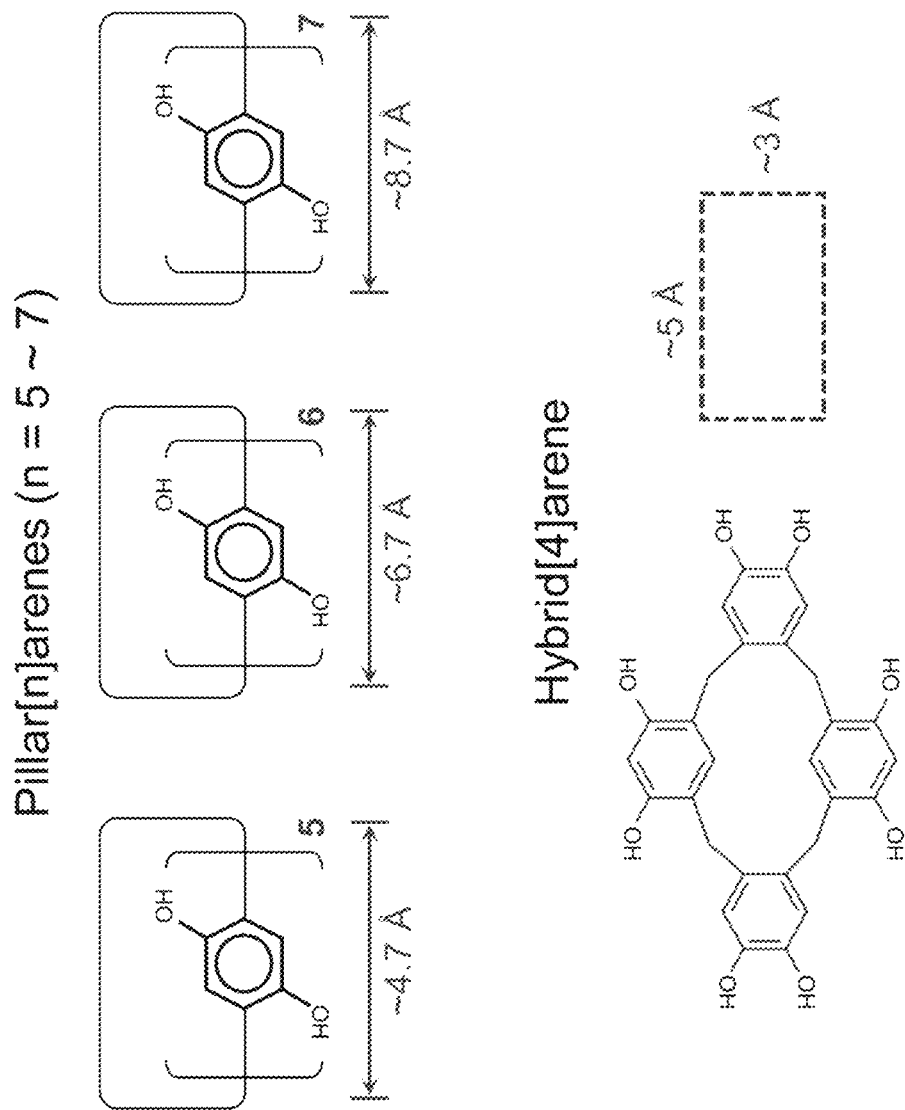
FIG. 7 depicts macrocycle candidates that can be used for tuning the microporosity of TFC membranes. Pillar[5]arene, pillar[6]arene and pillar[7]arene have ~4.7 Å, ~6.7 Å, and ~8.7 Å central cavity diameters, respectively. A series of hybrid[n]arenes can provide distinctive pore shapes at angstrom range such as rectangles with various dimensions.
Figure 8:
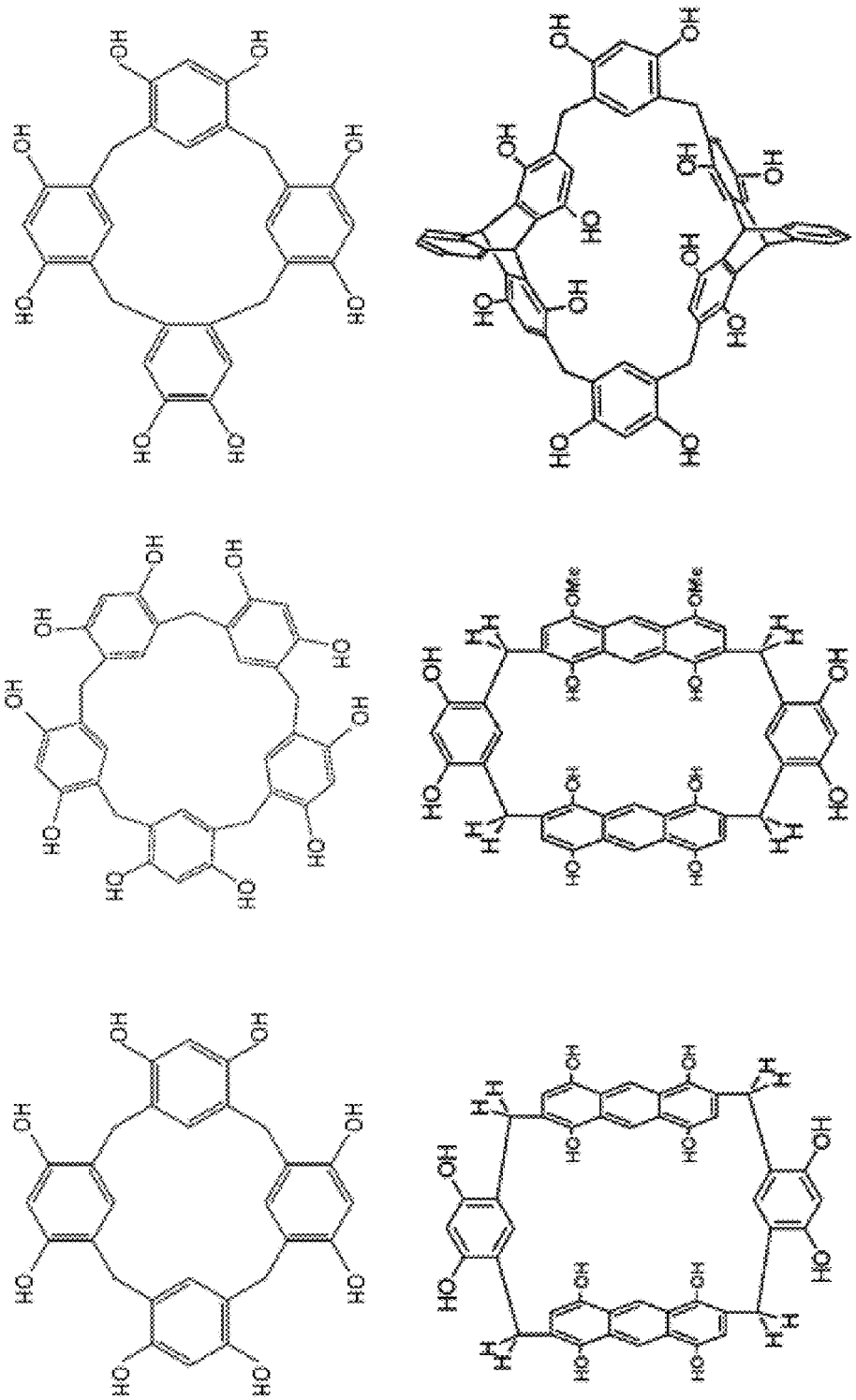
FIG. 8 depicts exemplary macrocycles that can be used for tuning the microporosity of TFC membranes.
Figure 9:
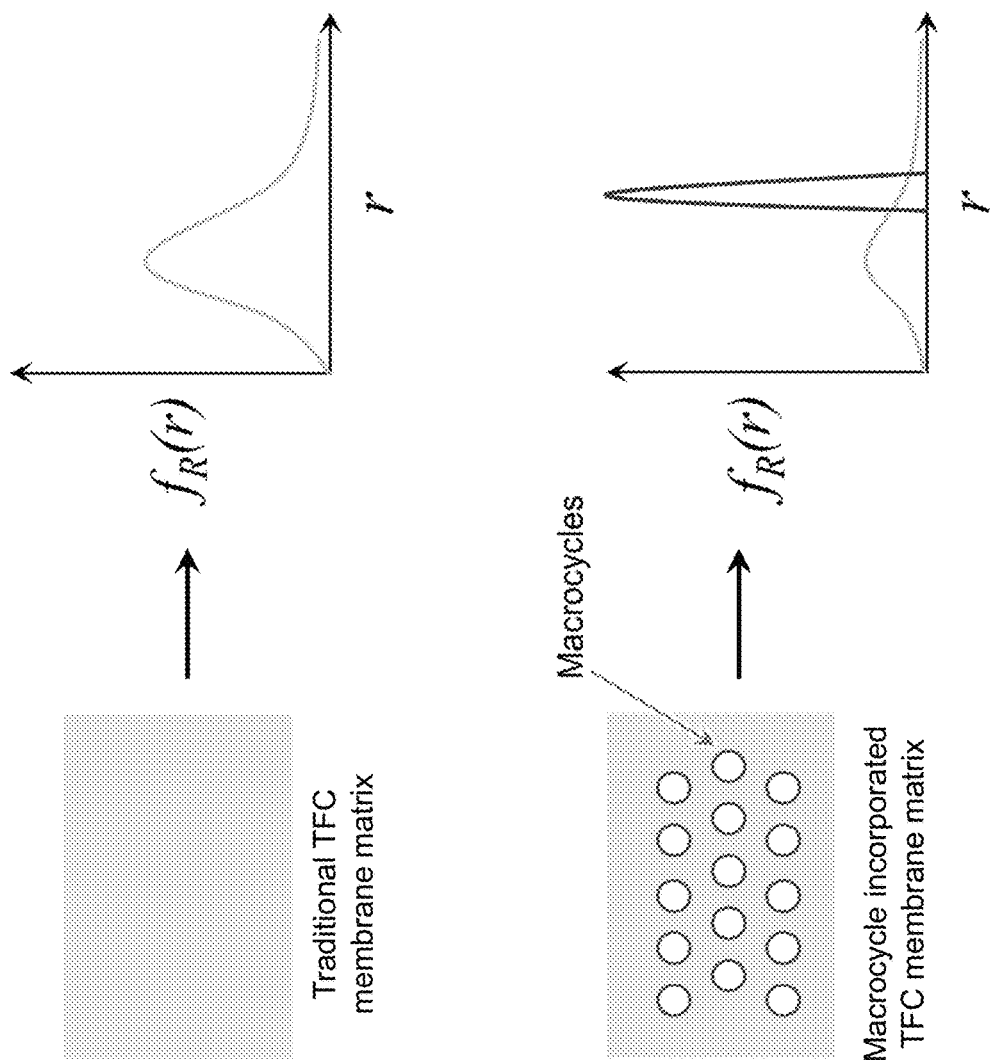
FIG. 9 depicts a schematic demonstrating the tunability of free void elements distribution via macrocycle incorporation wherein $f_R(r)$ is the probability function of pore size (r) distribution.
Figure 10B:
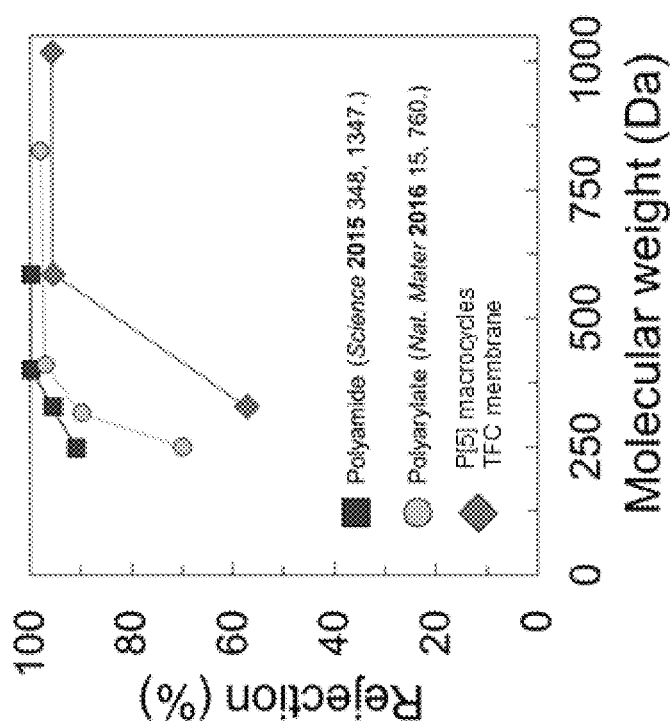
FIG. 10A and FIG. 10B, depicts a comparison of P[5] macrocycle TFC membrane solvent permeance and selectivity to other state-of-the-art membranes.
Figure 10A:
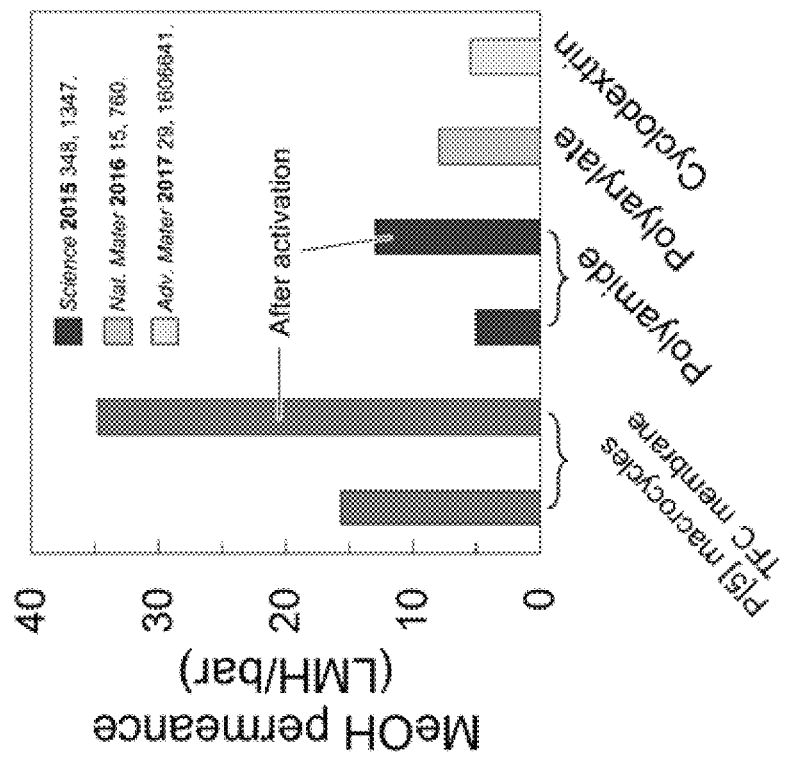

The present invention relates to TFC membranes comprising macrocycles, methods of making such TFC membranes, and methods of using such membranes. The present invention is based, in part, on the unexpected finding that the incorporation of macrocycles into TFC membranes results in enhanced solvent permeability and controllable molecular selectivity.

In one aspect, the invention provides a TFC membrane comprising a macrocycle such as a pillar[n]arene or hybrid [n]arene.

In another aspect, the invention provides a method of making a TFC membrane. In another aspect, the invention provides a method of tuning the microporosity of a TFC membrane.

Definitions

Unless defined otherwise, all technical and scientific terms used herein generally have the same meaning as commonly understood by one of ordinary skill in the art to which this invention belongs. Methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropylmethyl.

As used herein, the term "substituted alkyl" means alkyl, as defined above, substituted by one, two or three substituents selected from the group consisting of halogen, —OH, alkoxy, —NH$_2$, —N(CH$_3$)$_2$, —C(=O)OH, trifluoromethyl, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1-C_3)$ alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$-OH, —CH$_2$—CH$_2$—NH—CH$_3$, —CH$_2$—S—CH$_2$—C H$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

As used herein, the term "macrocycle" means a molecule containing a 4-member ring or larger.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Thin-Film Composite Membrane Composition

In one aspect, the present invention relates in part to a thin-film composite (TFC) membrane composition. In one embodiment, the TFC membrane comprises one or more channel elements. In one embodiment, the channels elements in the TFC membrane comprise one or small-molecule macrocycles. In one embodiment, the TFC membrane comprises a small-molecule macrocycle within a polymeric matrix element. In one embodiment, the small-molecule macrocycle within a polymeric matrix element is on a porous support. In one embodiment, the inventive TFC membranes provide tunable microporosity at the Angstrom scale. In one embodiment, the inventive TFC membranes comprise a small molecule pore element separated from a polymeric matrix element, thus enabling enhanced performance for gaseous, aqueous, organic solvent, and small molecule separation relative to leading membrane technologies. In one embodiment, the TFC membrane comprises one or more polymers. In one embodiment, the polymer comprises one or more inorganic polymers. In one embodiment, the polymer comprises one or more organic polymers. Exemplary organic polymers include, but are not limited to, polyamides, polyamines, polyimides polyesters, polyethers, polyethersulfones, polysulfones, polyacrylamides, and polycarbonates. In one embodiment, the TFC membrane comprises a polyamide. Exemplary polyamides include, but are not limited to, nylon 6, nylon 6,6, nylon 6,10, nylon 11, nylon 12, poly-para-phenylene terephthalamide, poly-meta-phenylene isophthalamide, polymers made from hexamethylenediamine and terephthalic acid, polymers made from m-phenylenediamine and 1,3,5-benzenetricarbonyl trihalides, polymers made from o-phenylenediamine and 1,3,5-benzenetricarbonyl trihalides, polymers made from p-phenylenediamine and 1,3,5-benzenetricarbonyltrihalides, polymers made from m-phenylenediamine and trimesic acid, polymers made from o-phenylenediamine and trimesic acid, and polymers made from p-phenylenediamine and trimesic acid.

In one embodiment, polymer comprises a polyamine. Exemplary polyamines include, but are not limited to, polyvinylamine, linear polyethyleneimine, branched polyethyleneimine, and polyallylamine.

In one embodiment, polymer comprises a polyimide. Exemplary polyimides include those made via a reaction between an anhydride and an amine. Exemplary anhydrides that can be used to form a polyimide include, but are not limited to, pyromellitic dianhydride, trimellitic anhydride, benzophenone tetracarboxylic dianhydride, oxydiphthalic anhydride, and hexafluorodianhydride. Exemplary amines that can be used to form a polyimide include, but are not limited to, 4,4'-oxydianiline, 4,4'-methylenedianiline, m-phenylenediamine, o-phenylenediamine, and p-phenylenediamine.

In one embodiment, the TFC membrane comprises a polyester. Exemplary polyesters include, but are not limited to, polymers made from 1,3-benzenediol and 1,3,5-benzenetricarbonyltrihalides, polymers made from 1,2-benzenediol and 1,3,5-benzenetricarbonyl trihalides, polymers made from 1,4-benzenediol and 1,3,5-benzenetricarbonyl trihalides, polymers made from 1,3,5-benzenetriol and 1,3,5-benzenetricarbonyl trihalides, polyglycolic acid, polylactic acid, polycaprolactone, polyhydroxyalkanoate, polyhydroxybutyrate, polyethylene adipate, polybutylene succinate, poly(3-hydroxybutyrate-co-3-hydroxyvalerate), polyethylene terephthalate, polybutylene terephthalate, polytrimethylene terephthalate, polyethylene napthalalte, and vectran.

In one embodiment, the TFC membrane comprises a polyethersulfone. In one embodiment, the polyethersulfone is a commercially available polyethersulfone.

Exemplary polyethersulfones include, but are not limited to, polymers made from dihalodiphenyl sulfones and dihydroxydiphenyl sulfone, polymers made from dihalodiphenyl sulfones and 4,4'-biphenol, E-6020P (BASF), Radel A-200 (Amoco Corporation), and Radel A-300 (Amoco Corporation).

In one embodiment, the TFC membrane comprises a polyacrylamide.

Exemplary polyacrylamides include, but are not limited to, poly(2-propenamide) (PAM), poly(N,N-dimethylacrylamide) (PDMA), poly(dimethyldiallylammonium chloride), poly(dimethyldiallylammonium bromide), poly(acrylooxyethyltrimethyl ammonium chloride), and poly(acrylooxyethyltrimethyl ammonium bromide). In one embodiment, the TFC membrane comprises polycarbonate.

In one embodiment, the TFC membrane comprises a macrocycle. Exemplary macrocycles include, but are not limited to, pillararenes, hybrid[n]arenes, calixarenes, heterocalixarenes, cucurbiturils, crown ethers, porphyrins, cyclodextrins, cryptands, spherands, carcerands, cyclophanes, and naturally occurring macrocycles. In one embodiment, the TFC membrane comprises one or more types of macrocycles. In one embodiment, the macrocycle comprises a cyclodextrin. Exemplary cyclodextrins include, but are not limited to, alpha-cyclodextrin, beta-cyclodextrin, and gamma-cyclodextrin. In one embodiment, the macrocycle comprises a pillararene. Exemplary pillararenes include, but are not limited to, pillar[4]arene, pillar[5]arene, pillar[6]arene, pillar[7]arene, and pillar[8]arene, peptide-appended pillar[4]arenes (PAP[4]), peptide-appended pillar[5]arenes (PAP[5]), peptide-appended pillar[6]arenes (PAP[6]), peptide-appended pillar[7]arenes (PAP[7]), and peptide-appended pillar[8]arenes (PAP[8]). In one embodiment, the macrocycle comprises a hybrid[n]arene. Exemplary hybrid [n]arenes include, but are not limited to, those made from the condensation of 1,4-dimethoxybenzene, 1,3,5-trimethoxybenzene, and formaldehyde; those made from the reaction of 1,4,5,8-tetramethoxyanthracene, 1,3-dimethoxybenzene, and trifluoroacetic acid; and those made from 1,6-dimethoxynapthalene and 1,3-dimethoxybenzene.

In one embodiment, the macrocycle is selected from the group consisting of:

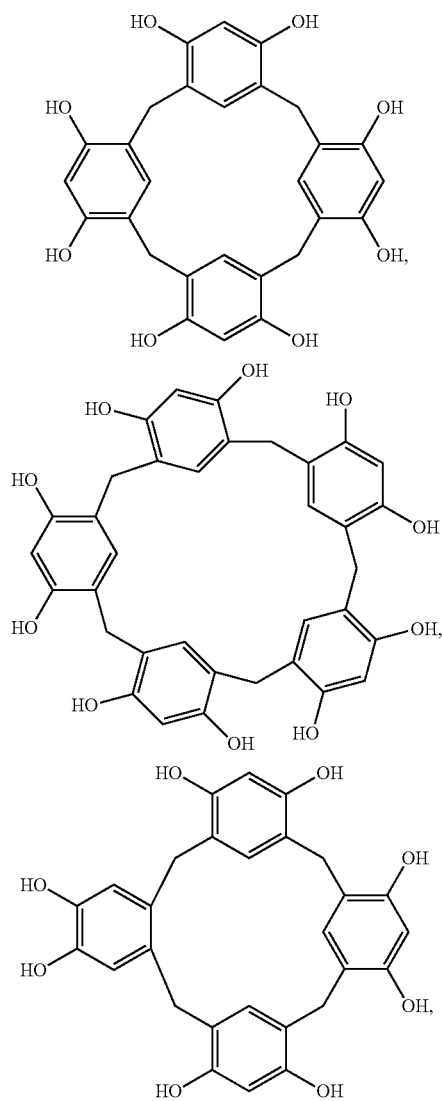

-continued

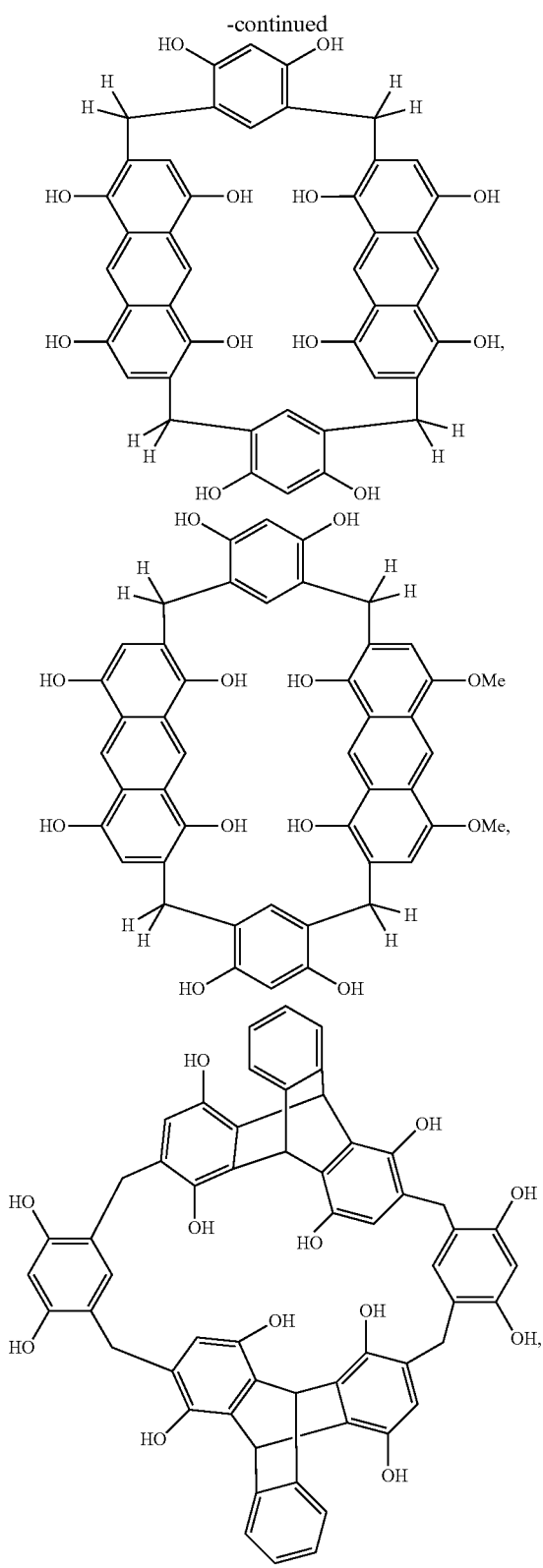

and combinations thereof.

In one embodiment, the macrocycle is a naturally occurring macrocycle. Exemplary naturally occurring macrocycles include, but are not limited to, FK-506, erythromycin A, vancomycin, epothilone B, rafamycins, ziconotide, and outer membrane protein F (OmpF). In one embodiment, the TFC membrane comprises more than one type of macrocycle.

In one embodiment, the TFC membrane comprises one or more polymers and one or more macrocycles. In one embodiment, the one or more macrocycles are incorporated into the TFC membrane to form pores. In one embodiment, the pores have a diameter between 1 and 20 Å. In one embodiment, the pores have a diameter between 1 and 18 Å. In one embodiment, the pores have a diameter between 1 and 16 Å. In one embodiment, the pores have a diameter between 1 and 14 Å. In one embodiment, the pores have a diameter between 1 and 12 Å. In one embodiment, the pores have a diameter between 1 and 10 Å. In one embodiment, the pores have a diameter between 2 and 9.5 Å. In one embodiment, the pores are circular in shape. In one embodiment, the pores are rectangular in shape. In one embodiment, the macrocycle comprises a pillar[5]arene having a pore diameter of about 4.7 Å. In one embodiment, the macrocycle comprises a pillar[6]arene having a pore diameter of about 6.7 Å. In one embodiment, the macrocycle comprises a pillar[8]arene having a pore diameter of about 8.7 Å.

In one embodiment, the macrocycles in the TFC membrane are both highly uniform and tunable, enabling a solution flow mechanism that enhances solvent permeability while retaining molecular selectivity. In one embodiment, the TFC membrane comprising macrocycles exhibits over twice the permeance of leading membrane technologies with comparable selectivity.

In one embodiment, the macrocycle pores have a specific size which allow for host-guest interactions with a specific species in a mixture over all other components in the mixture. This host-guest interaction allows for the separation of a specific species from the mixture over all other components in the mixture. In one embodiment, the environment in the pores of the macrocycles is electron rich. In one embodiment, the electron rich environment of the macrocycle pores permits only electron poor species to enter and bind to the macrocycle pore. In one embodiment, the electron rich environment of the macrocycle pores allow for a host-guest interaction between the macrocycle pores and electron poor linear alkanes. In one embodiment, the electron rich environment of the macrocycle pores prevents electron rich alkenes from entering and binding the macrocycle pore. In one embodiment, the binding between the electron poor linear alkanes and electron rich macrocycle pores is weak enough that a second linear alkane can displace the first linear alkane when the second linear alkane enters the macrocycle pore. In one embodiment, the electron rich macrocycle pore is the pore of a pillararene macrocycle.

In one embodiment, the TFC membrane is between 1 nm and 0.5 mm thick. In one embodiment, the TFC membrane is between 1 nm and 0.4 mm thick. In one embodiment, the TFC membrane is between 1 nm and 0.3 mm thick. In one embodiment, the TFC membrane is between 1 nm and 0.2 mm thick. In one embodiment, the TFC membrane is between 1 nm and 0.1 mm thick. In one embodiment, the TFC membrane is between 1 nm and 90 μm thick. In one embodiment, the TFC membrane is between 1 nm and 80 μm thick. In one embodiment, the TFC membrane is between 1 nm and 70 μm thick. In one embodiment, the TFC membrane is between 1 nm and 60 μm thick. In one embodiment, the TFC membrane is between 1 nm and 50 μm thick. In one embodiment, the TFC membrane is between 1 nm and 40 μm thick. In one embodiment, the TFC membrane is between 1 nm and 30 μm thick. In one embodiment, the TFC membrane is between 1 nm and 20 μm thick. In one embodiment, the TFC membrane is between 1 nm and 10 µm thick. In one embodiment, the TFC membrane is between 1 nm and 1000 nm thick. In one embodiment, the TFC membrane comprises multiple membrane layers.

In one embodiment, the TFC membrane comprises a support. Exemplary supports include, but are not limited to, alumina, silica, carbon black, carbon nanotubes, ceramic, cellulose, and organic polymers. In one embodiment, the support comprises one or more organic polymers. The organic polymer may be any exemplary polymer described elsewhere herein. In one embodiment, the support comprises a phase separation polymer. Exemplary phase separation polymers include, but are not limited to, polyethersulfone, polyphenylenesulfone, polyphenylenesulfidesulfone, polyacrylonitrile, cellulose ester, polyphenyleneoxide, polypropylene, polyvinylidene fluoride, polyvinylidene difluoride, polyvinylchloride, polyarylsulfone, polyphenylene sulfone, polyether ether ketone, polysulfone, polyamide, polyimide, and a combination thereof. In one embodiment, the support comprises a polycarbonate. In one embodiment, the support comprises nylon. In one embodiment, the support comprises Teflon. In one embodiment, the support comprises polypropylene. In one embodiment, the support comprises polyethylene. In one embodiment, the support comprises ethylene chlorotrifluoroethylene (ECTFE). In one embodiment, the support is porous.

In one embodiment, the support is between 1 µm and 10 mm thick. In one embodiment, the support is between 1 µm and 9 mm thick. In one embodiment, the support is between 1 µm and 8 mm thick. In one embodiment, the support is between 1 µm and 7 mm thick. In one embodiment, the support is between 1 µm and 0.6 mm thick. In one embodiment, the support is between 1 µm and 6 mm thick. In one embodiment, the support is between 1 µm and 5 mm thick. In one embodiment, the support is between 1 µm and 4 mm thick. In one embodiment, the support is between 1 µm and 3 mm thick. In one embodiment, the support is between 1 µm and 4 mm thick. In one embodiment, the support is between 1 µm and 2 mm thick. In one embodiment, the support is between 1 µm and 4 mm thick. In one embodiment, the support is between 1 µm and 1 mm thick.

In one embodiment, the TFC membrane comprises one or more types/sizes of macrocycles that undergo specific interactions with one or more species from a mixture of two or more species. This specific interaction permits only specific species to pass through the pores in the macrocycle. In one embodiment, this specific interaction permits the separation of linear alkanes from a mixture comprising linear alkanes, branched alkanes, alkenes, and/or cyclic alkanes. In one embodiment, the TFC membrane comprises a pillararene macrocycle which permits the passage of only linear alkanes through the pores of the macrocycle from a mixture comprising linear alkanes, branched alkanes, alkenes, and/or cyclic alkanes. In one embodiment, the TFC membrane comprises a pillararene macrocycle which permits the passage of only n-butane through the pores of the macrocycle from a mixture n-butane, iso-butane, iso-butene, and 1-butene.

Method of Making Thin-Film Composite

The present invention relates in part to a method of making a TFC membrane. Exemplary process 100 is shown in FIG. 1. In step 110, a solution comprising a first organic species and, optionally, a second organic species is provided. In step 120, a macrocycle is provided. In step 130, the solution comprising the first organic species and the macrocycle are mixed to form a mixture. In step 140, the mixture forms a TFC membrane.

In step 110, a solution comprising a first organic species is provided. In one embodiment, the first organic species is an organic polymer. The polymer may be any polymer exemplified elsewhere herein. In another embodiment, the first organic species is a monomer. Exemplary monomers include, but are not limited to, hexamethylenediamine; m-phenylenediamine; o-phenylenediamine; p-phenylenediamine; ethylenediamine; xylylenediamine; piperazine; isophthaloyl halides; 1,3,5-cyclohexanetricarbonyl halides; tetrahydrofuran-1,2,3,4-tetracarbonyl halides; 1,3,5-benzenetricarbonyl trihalides; acrylamide; cyclohexane diamines; chlorophenylene diamines (e.g. 4- or 5-chlorometaphenylene diamine); benzene triamines (e.g. 1,3,5-benzene triamine); bis (aminobenzyl) aniline; tetra amino benzenes; tetra amino biphenyls (e.g. 3,3',4,4,' tetra amino biphenyl; tetrakis (aminomethyl) methane; methyl piperazine; dimethyl piperazine (e.g. 2,5-dimethyl piperazine); homopiperazine; diamino-diphenyl methanes; N,N'-diphenyl ethylenediamine; aminobenzamides (e.g. 4-amino-benzamide); aminobenzhydrazides; bis(aminobenzyl)anilines; 1,3-benzenediol; 1,2-benzenediol; 1,4-benzenediol; dihydroxyanthraquinone; bis(alkylamino)phenylenediamines (e.g. N,N'-dimethyl-1,3-phenylenediamine) melamine; mono(alkylamino)phenylenediamines (e.g. N-methyl-1,3-phenylenediamine); aminomethylpiperidine; triamino-hydroxy-pyrimidines (e.g. 2,4,5-triamino-6-hydroxy pyrimidine or 4,5,6-triamino-2-hydroxy pyrimidine); triaminopyrimidines (e.g. 2,4,6-triamino-pyrimidine or 4,5,6-triamino-pyrimidine); tetra amino pyrimidines (e.g. 2,4,5,6-tetra amino pyrimidine); para rosaniline; tris (aziridinyl) propionates (e.g. trimethylol propane-tris(β-(N-aziridinyl) propionate or penta-erythritol-tris β(N-aziridinyl) propionate); tetra amino biphenyls; bis(amino benzyl)anilines; benzene tricarboxylic acid halides (e.g. trimesoyl chloride or trimellitic acid trichloride); cyclohexane dicarboxylic acid halides (e.g. 1,3-cyclohexane dicarboxylic acid chloride or 1,4-cyclohexane dicarboxylic acid chloride); cyclohexane tricarboxylic acid halides (e.g. cis-1,3,5-cyclohexane tricarboxylic acid trichloride); pyridine dicarboxylic acid halides (e.g. quinolinic acid dichloride or dipicolinic acid dichloride); trimellitic anhydride acid halides; benzene tetra carboxylic acid halides (e.g. pyromellitic acid tetra chloride); pyromellitic acid dianhydride; pyridine tricarboxylic acid halides; sebacic acid halides; azelaic acid halides; adipic acid halides; dodecanedioc acid halides; toluene diisocyanate; methylene bis (phenyl isocyanates); naphthalene diisocyanates; bitolyl diisocyanates;

hexamethylene diisocyanate; phenylene diisocyanates; isocyanato benzene dicarboxylic acid halides (e.g. 5-isocyanato isophthaloyl chloride); haloformyloxy benzene dicarboxylic acid halides (e.g. 5-chloroformyloxy isophthaloyl chloride); dihalosulfonyl benzenes (e.g. 1,3-benzene disulfonic acid chloride); halosulfonyl benzene dicarboxylic acid halides (e.g. 3-chlorosulfonyl isophthaloyl chloride); cyclobutane dicarboxylic acid halide; piperazine —N—N'-diformyl halides; dimethyl piperazine —N,N-diformyl halides; xylylene glycol dihaloformates; benzene diol dihaloformates; benzene triol trihaloformates; phosgene; diphosgene; triphosgene; N,N'-carbonyl diimidazole; isocyanuric acid —N,N',N"-triacetyl halides; isocyanuric acid-N,N',N" tripropionyl halides; and cyclopentane tetracarboxylic acid halides.

In one embodiment, the solution comprising the first organic species is an aqueous solution comprising one or more aqueous solvents. Exemplary aqueous solvents include, but are not limited to, water, distilled water, and deionized water. In one embodiment, the aqueous solution comprises a base. Exemplary bases include, but are not limited to, sodium hydroxide, potassium hydroxide, magnesium hydroxide, calcium hydroxide, calcium carbonate, and sodium bicarbonate. In one embodiment, the aqueous solution comprises an acid. Exemplary acids include, but are not limited to, hydrochloric acid, acetic acid, sulfuric acid, nitric acid, hydrobromic acid, perchloric acid, chloric acid, phosphoric acid, and citric acid.

In one embodiment, the solution comprising the first organic species is an organic solution comprising one or more organic solvents. Exemplary organic solvents include, but are not limited to, hexane, pentane, dichloromethane, acetone, diethyl ether, tetrahydrofuran, methanol, ethanol, isopropanol, 1-propanol, n-butanol, sec-butanol, isobutanol, tert-butanol, benzene, and toluene. In some embodiments, the organic solvent is an ionic liquid. Exemplary ionic liquids include, but are not limited to, 1-butyl-3-methylimidazolium salts (e.g. hexafluorophosphate, tetrafluoroborate, acetate, hydrogen sulfate, chloride, bromide, fluoride, methanesulfonate, methyl sulfate, ethyl sulfate, tetrachloroaluminate); 1-ethyl-3-methylimidazolium salts (e.g. hydrogen sulfate, thiocyanate, methanesulfonate, tetrachloroaluminate, thiocyanate, acetate, chloride, bromide, fluoride); 1-ethyl-2,3-dimethylimidazolium ethyl sulfate; 1-methylimidazolium salts (e.g. chloride, bromide, fluoride, hydrogen sulfate); 1,2,3-trimethylimidazolium methyl sulfate; and tributylmethylammonium methyl sulfate. In one embodiment, the solution comprising the first organic species comprises both an aqueous solvent and an organic solvent. In one embodiment, the solution comprising the first organic species comprises 50% by volume of an aqueous solvent and 50% by volume of an organic solvent.

In one embodiment, the second organic species is a monomer. The monomer may be any exemplary monomer described elsewhere herein. In one embodiment, the second organic species is mixed with an aqueous solution. The aqueous solution may be any exemplary aqueous solution described elsewhere herein. In another embodiment, the second organic species is mixed with an organic solvent. The organic solvent may be any exemplary organic solvent described elsewhere herein.

In step 120, a macrocycle is provided. The macrocycle may be any exemplary macrocycle, or a combination of macrocycles, described elsewhere herein.

In step 130, the solution comprising the first organic species and the macrocycle are mixed to form a mixture. In one embodiment, the macrocycle is added to the solution comprising the first organic species. In one embodiment, the macrocycle is added all at once. In one embodiment, the macrocycle is added dropwise. In one embodiment, the mixture is stirred. In one embodiment, the mixture is vortexed. In one embodiment, the mixture is sonicated. In one embodiment, the mixture is shaken. In one embodiment, the mixture is heated. In one embodiment, the mixture is cooled. In one embodiment, the mixture is vortexed and sonicated. In one embodiment, the mixture is sonicated for 1 minute to 60 minutes. In one embodiment, the mixture is sonicated for 1 minute to 50 minutes. In one embodiment, the mixture is sonicated for 1 minute to 40 minutes. In one embodiment, the mixture is sonicated for 1 minute to 30 minutes. In one embodiment, the mixture is sonicated for 1 minute to 20 minutes. In one embodiment, the mixture is sonicated for 1 minute to 10 minutes.

In some embodiments, the step of mixing the first organic species and the macrocycle further comprises step 132, wherein a support is added to the mixture. The support may be any exemplary support described elsewhere herein. In some embodiments, the support is porous.

In one embodiment, the support is conditioned before being added to the mixture. In one embodiment, the support is conditioned by contacting the support with a solution of the first organic species, wherein the first organic species is a monomer, and macrocycle. In one embodiment, the support is conditioned by contacting the support with the solution for 1 minute to 60 minutes. In one embodiment, the support is conditioned by contacting the support with the solution for 1 minute to 50 minutes. In one embodiment, the support is conditioned by contacting the support with the solution for 1 minute to 40 minutes. In one embodiment, the support is conditioned by contacting the support with the solution for 1 minute to 30 minutes. In one embodiment, the support is conditioned by contacting the support with the solution for 1 minute to 20 minutes. In one embodiment, the support is conditioned by contacting the support with the solution for 1 minute to 10 minutes. In one embodiment, the conditioned support, lacking the second organic species, is then added, in step 132, to a mixture comprising the first organic species, the second organic species, and the macrocycle.

In one embodiment, the support is activated by irradiating the support. In one embodiment, the support is irradiated with visible light. In one embodiment, the support is irradiated with UV light. In one embodiment, the support is activated by contacting the support with ozone. In one embodiment, the support is both contacted with ozone and irradiated.

In one embodiment, the support is contacted with ozone and irradiated for 10 seconds to 30 minutes. In one embodiment, the support is contacted with ozone and irradiated for 10 seconds to 25 minutes. In one embodiment, the support is contacted with ozone and irradiated for 10 seconds to 20 minutes. In one embodiment, the support is contacted with ozone and irradiated for 10 seconds to 15 minutes. In one embodiment, the support is contacted with ozone and irradiated for 10 seconds to 10 minutes. In one embodiment, the support is contacted with ozone and irradiated for 10 seconds to 5 minutes. In one embodiment, the support is contacted with ozone and irradiated for 10 seconds to 2 minutes. In one embodiment, the support is contacted with ozone and irradiated for 10 seconds to 45 seconds.

In step 140, the mixture forms a TFC membrane. In one embodiment, the TFC membrane is formed on the support. In one embodiment, the TFC membrane forms multiple layers on the support. In one embodiment, the mixture undergoes a polymerization reaction to form a TFC membrane. In one embodiment, the polymerization reaction occurs in 1 to 30 minutes. In one embodiment, the polymerization reaction occurs in 1 to 25 minutes. In one embodiment, the polymerization reaction occurs in 1 to 20 minutes. In one embodiment, the polymerization reaction occurs in 1 to 15 minutes. In one embodiment, the polymerization reaction occurs in 1 to 10 minutes. In one embodiment, the polymerization reaction occurs in 1 to 5 minutes. In one embodiment, the polymerization reaction forms a TFC membrane on the support. In one embodiment, the polymerization reaction forms multiple layers of the TFC membrane on the support. In one embodiment, the polymerization reaction is an interfacial polymerization reaction.

Method of Separating Gas or Liquid

The present invention relates in part to a method of separating a first species from a mixture of the first species and a second species. In one embodiment, the method comprises the steps of: 1) applying the mixture to a feed side of a TFC membrane; 2) causing the first species to pass through the TFC membrane; and 3) collecting the first species from an opposite side of the TFC membrane or the second species from the feed side of the TFC membrane.

In one embodiment, elevated pressures are used to cause the first species to pass through the TFC membrane. In one embodiment, reduced pressures are used to cause the first species to pass through the TFC membrane. In one embodiment, the pressure is between −1 bar and 1000 bar. In one embodiment, the pressure is between −1 bar and 900 bar. In one embodiment, the pressure is between −1 bar and 800 bar. In one embodiment, the pressure is between −1 bar and 700 bar. In one embodiment, the pressure is between −1 bar and 600 bar. In one embodiment, the pressure is between −1 bar and 500 bar.

In one embodiment, the first species is passed through the TFC membrane under a reduced temperature. In one embodiment, the first species is passed through the TFC membrane under an elevated temperature. In one embodiment, the temperature is between 0° C. and 500° C. In one embodiment, the temperature is between 0° C. and 450° C. In one embodiment, the temperature is between 0° C. and 400° C. In one embodiment, the temperature is between 0° C. and 350° C. In one embodiment, the temperature is between 0° C. and 300° C. In one embodiment, the temperature is between 0° C. and 250° C. In one embodiment, the temperature is between 0° C. and 200° C. In one embodiment, the temperature is between 0° C. and 150° C.

In one embodiment, the first species is a gas. In one embodiment, the first species is a liquid. In one embodiment, the second species is a gas. In one embodiment, the second species is a liquid. In one embodiment, the mixture contains more than two species. Exemplary separations include, but are not limited to, linear hydrocarbons from a mixture comprising linear hydrocarbons, branched hydrocarbons, and/or cyclic hydrocarbons; ethane from ethylene, propane from propylene, hydrogen sulfide from nitrogen, hydrogen sulfide from methane, hydrogen sulfide from carbon dioxide, carbon dioxide from nitrogen, carbon dioxide from methane, carbon dioxide from oxygen, carbon dioxide from hydrogen, sulfur dioxide from nitrogen, ammonia from nitrogen, water vapor from air, hydrogen from hydrocarbons, hydrogen from nitrogen, hydrogen from carbon monoxide, carbon dioxide from natural gas, water from natural gas, hydrogen sulfide from natural gas, oxygen from air, nitrogen from air, alcohols from water, phenols from water, chlorinated hydrocarbons from water, hydrocarbons from water, pyridine from water, ketones from water, sodium chloride from water, paraffins from olefins, ethyl acetate from ethanol, diethyl ether from ethanol, acetic acid from ethanol, benzene from ethanol, chloroform from ethanol, chloroform from methanol, acetone from isopropyl ether, allyl alcohol from allyl ether, allyl alcohol from cyclohexane, butanol from butyl acetate, butanol from 1-butylether, ethanol from ethylbutyl ether, propylacetate from propanol, isopropyl ether from isopropanol, volatile organic compounds from air, small molecule compounds from water, and low molecular weight compounds/oligomers from organic solvents.

In one embodiment, the method comprises the separation of linear hydrocarbons from branched hydrocarbons. In one embodiment, the linear hydrocarbon is a $C_4$ hydrocarbon and the branched hydrocarbon is one or more branched $C_4$ hydrocarbons.

In one embodiment, the method comprises the separation of linear alkanes from branched alkanes. In one embodiment, the method comprises the separation of linear alkanes from branched alkenes. In one embodiment, the method comprises the separation of linear alkanes from a mixture of linear alkanes, branched alkanes, and branched alkenes.

In one embodiment, the method comprises the separation of n-butane from a mixture of n-butane, 1-butene, iso-butane, and iso-butene. In one embodiment, the method comprises the separation of n-butane from a mixture of n-butane, 1-butene, and iso-butane. In one embodiment, the method comprises the separation of n-butane from a mixture of n-butane, 1-butene, and iso-butene. In one embodiment, the method comprises the separation of n-butane from a mixture of n-butane, iso-butane, and iso-butene. In one embodiment, the method comprises the separation n-butane from iso-butane. In one embodiment, the method comprises the separation of n-butane from 1-butene. In one embodiment, the method comprises the separation of n-butane from iso-butene.

In one embodiment, the method comprises the separation of ethane from ethylene.

In one embodiment, the method comprises the separation of propane from propylene.

Method of Separating a Linear Hydrocarbon from a Branched Hydrocarbon

The present also invention relates in part to a method of separating a linear hydrocarbon from a mixture of the linear hydrocarbon and a branched hydrocarbon. In one embodiment, the method comprises the steps of: 1) applying a mixture comprising a linear hydrocarbon and a branched hydrocarbon to a feed side of a TFC membrane; 2) causing the linear hydrocarbon to pass through the TFC membrane; and 3) collecting the linear hydrocarbon from an opposite side of the TFC membrane or the branched hydrocarbon from the feed side of the TFC membrane.

In one embodiment, elevated pressures are used to cause the linear hydrocarbon to pass through the TFC membrane. Exemplary pressures are described elsewhere herein.

The mixture in step 1) can comprise any mixture of linear hydrocarbons and branched hydrocarbons known to a person of skill in the art. In one embodiment, the branched hydrocarbon comprises branched hydrocarbons and/or cyclic hydrocarbons. In one embodiment, the branched hydrocarbons comprise branched alkanes and/or alkenes. In one embodiment, the cyclic hydrocarbons comprise cyclic alkanes and/or cyclic alkenes. In one embodiment, the linear hydrocarbon comprises a linear alkane. The linear alkane can comprise any number of carbons known to a person of skill in the art. In one embodiment, the linear alkane is a $C_2$ alkane. In one embodiment, the linear alkane is a $C_3$ alkane. In one embodiment, the linear alkane is a $C_4$ alkane.

In one embodiment, the linear hydrocarbon is n-butane and the branched hydrocarbon is iso-butane, iso-butene, and/or 1-butene. In one embodiment, the linear hydrocarbon is ethane and the branched hydrocarbon is ethylene. In one embodiment, the linear hydrocarbon is propane and the branched hydrocarbon is propylene.

In one embodiment, the TFC membrane of steps 1)-3) comprises macrocycles. Exemplary macrocycles are described elsewhere herein. In one embodiment, the macrocycles comprise pores. In one embodiment, the macrocycle pores have a specific size which allow for host-guest interactions with a linear hydrocarbon in the mixture over all other components in the mixture, including non-linear hydrocarbons. This host-guest interaction allows for the separation of the linear hydrocarbon from the mixture over all other components in the mixture.

In one embodiment, the environment in the pores of the macrocycles is electron rich. In one embodiment, the electron rich environment of the macrocycle pores permits only the electron poor linear hydrocarbons to enter and bind to the macrocycle pore. In one embodiment, the electron rich environment of the macrocycle pores allow for a host-guest interaction between the macrocycle pores and electron poor linear hydrocarbons. In one embodiment, the electron rich environment of the macrocycle pores prevents electron rich branched alkenes from entering and binding the macrocycle pore. In one embodiment, the binding between the electron poor linear hydrocarbon and electron rich macrocycle pores is weak enough that a second linear hydrocarbon can displace the first linear hydrocarbon when the second linear alkane enters the macrocycle pore. In one embodiment, the electron rich macrocycle pore is the pore of a pillararene macrocycle. In one embodiment, the electron rich macrocycle pore is the pore of a pillar[5]arene macrocycle.

In one embodiment, the TFC membrane of steps 1)-3) comprises a polymeric matrix wherein the macrocycle pores are distributed. The polymeric matrix can comprise any polymer known to a person of skill in the art. Exemplary polymers are described elsewhere herein.

Method of Enhancing Solvent Permeability of a TFC Membrane

In one aspect, the present invention relates to a method of enhancing the solvent permeability of a TFC membrane. In one embodiment, the method comprises contacting a TFC membrane with a solvent comprising a mixture of at least a first species and a second species. In one embodiment, the method comprises separating the at least first species and second species. In one embodiment, the TFC membrane comprises macrocycles. In one embodiment, the method comprises separating the at least first species and second species by exposing the mixture to a TFC membrane comprising macrocycles of a size such that one or more of the species in the mixture cannot pass though openings created by the macrocycles.

The first and second species may be any species disclosed in the exemplary separations elsewhere herein. The TFC membrane may be any exemplary TFC membrane described elsewhere herein. In one embodiment, the solvent permeability is enhanced by the incorporation of macrocycles into the TFC membrane. The macrocycle may be any exemplary macrocycle described elsewhere herein.

Method of Controlling Molecular Sensitivity of TFC Membranes

In one aspect, the present invention relates to a method of controlling the molecular sensitivity of TFC membranes. In one embodiment, the method comprises contacting a TFC membrane with a mixture comprising at least a first species and a second species. In one embodiment, the method comprises separating the at least first species and second species. In one embodiment, the TFC membrane comprises macrocycles. In one embodiment, the method comprises separating the at least first species and second species by exposing the mixture to a TFC membrane comprising macrocycles of a size such that one or more of the species in the mixture cannot pass though pores created by the macrocycles.

The first and second species may be any species disclosed in the exemplary separations elsewhere herein. The TFC membrane may be any exemplary TFC membrane described elsewhere herein. In one embodiment, the molecular sensitivity is controlled by the incorporation of macrocycles into the TFC membrane. The macrocycle may be any exemplary macrocycle described elsewhere herein.

In one embodiment, the first species comprises a linear hydrocarbon which passes though the pores of the macrocycle in the TFC membrane. Exemplary linear hydrocarbons are described elsewhere herein. In one embodiment, the second species comprises a branched hydrocarbon. Exemplary branched hydrocarbons are described elsewhere herein. In one embodiment, the size, shape, and/or distribution of the macrocycles (and their associated pores) is highly uniform and timable, enabling a solution flow mechanism that enhances solvent permeability while retaining molecular selectivity. In one embodiment, the inventive TFC membranes exhibit over twice the permeance of leading membrane technologies with comparable selectivity.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods.

The following working examples therefore, specifically point out the preferred embodiments of the present invention, and are not to be construed as limiting in any way the remainder of the disclosure.

Example 1. Permeability and Selectivity Studies of TFC Membranes Incorporating Macrocycles Macrocycle TFC membranes can be prepared via conventional IP method by simply adding macrocycles into first monomer solution at membrane fabrication step. Incorporated macrocycles provide unitary free volume elements inside the polymer which result in high selectivity at angstrom scale separation. Macrocycle candidates that can be used for tuning the microporosity of TFC membranes include pillar[n]arenes and hybrid[n]arenes. Pillar[5]arene, pillar[6]arene and pillar[7]arene have ~4.7 Å, ~6.7 Å, and ~8.7 Å central cavity diameters, respectively. A series of hybrid[n]arenes can provide distinctive pore shapes at angstrom range such as rectangles with various dimensions.

Table 1 shows the ultrafiltration substrate, TFC, water permeability and salt rejection for each trial. PES refers to polyethersulfone membrane, MPD refers to m-phenylenediamine, PC refers to polycarbonate, PEI refers to polyethylenimine, and RO refers to reverse osmosis.

TABLE 1

| Trial | Ultrafiltration substrate | Thin film composite (TFC) | Water permeability (LMH/bar) | Salt rejection (NaCl) |
|---|---|---|---|---|
| 1 | PES (30 nm) | MPD (1% w/v) TMC (1% w/v) | 25.56 | Less than 10% |
| 2 | PES (30 nm) | MPD (1% w/v) TMC (1% w/v) | Faster than #1 | 15% |

TABLE 1-continued

| Trial | Ultrafiltration substrate | Thin film composite (TFC) | Water permeability (LMH/bar) | Salt rejection (NaCl) |
|---|---|---|---|---|
| 3 | PES (30 nm) | MPD (1% w/v) TMC (1% w/v) | Faster than #1 | Not expected |
| 4 | PES (30 nm) | MPD (2% w/v) TMC (1% w/v) | Slower than #1 | 16% |
| 5 | PES (30 nm) | MPD (1% w/v) TMC (1% w/v) PAP[5] crystal | Faster than #1 | Not expected |
| 6 | PES (30 nm) | Polyacrylamide gel PAP[5] crystal | Faster than #1 | Not expected |
| 7 | PES (30 nm) | MPD (1% w/v) TMC (0.1% w/v) | Faster than RO | 10% |
| 8 | PES (30 nm) | MPD (2% w/v) TMC (1% w/v) | Little faster than RO | 60% |
| 9 | PES (30 nm) | MPD (2% w/v) TMC (1% w/v) | Little faster than RO | 40% |
| 10 | PES (30 nm) | MPD (2% w/v) TMC (1% w/v) PAP[5] crystal (crosslinked) | Very fast, similar to PES membrane | Not expected |
| 11 | PC (100 nm) | PEI + OmpF crystal | 7.0 | ~15% (PEG600) |
| 12 | PC (50 nm) | PEI + OmpF crystal | 1.8 | PEG$_{300}$: 33% PEG$_{600}$: 56% PEG$_{1100}$: 68% PEG$_{4000}$: 84% |
| 13 | PES (30 nm) | MPD (2% w/v) TMC (0.1% w/v) | 1.11 | 1.11 |
| 14 | PES (30 nm) | MPD (0.1% w/v) TMC (0.5% w/v) in Ionic liquid (IL) | NA | NA |
| 15 | PES (30 nm) | MPD (0.1% w/v) TMC (0.5% w/v) in IL | 1.31 | 1.31 |
| 16 | PES (30 nm) | PEI PAP[5] crystal MPD (0.1% w/v) TMC (0.5% w/v) in IL | 55.3 | 55.3 |
| 17 | PC (50 nm) | PEI + PAP[5] crystal | 1.67 | 1.67 |
| 18 | PC (50 nm) | 0.1% MPD + PAP[5] crystal | 0.96 | 0.96 |
| 19 | 19 | PES (30 nm) | PAP[5] crystal MPD 2% TMC 0.1% | 0.558 (300 psi) |
| 20 | 20 | PES (30 nm) | PAP[5] crystal MPD 2% TMC 0.1% | 0.458 (300 psi) |
| 21 | 21 | PES (30 nm) | PAP[5] crystal MPD 1% TMC 0.05% | To be tested |
| 22 | 22 | PES (30 nm) | PAP[5] crystal MPD 0.5% TMC 0.025% | To be tested |
| 23 | 23 | PES (30 nm) | PAP[5] crystal MPD 0.1% TMC 0.005% | To be tested |
| 24 | 24 | PES (30 nm) | PAP[5] crystal MPD 0.1% TMC 0.005% | 9.9 |
| 25 | PES (30 nm) | PAP[5] crystal MPD 0.1% TMC 0.005% | 632 | PEG$_{300}$: 0% PEG$_{600}$: 8% PEG$_{1100}$: 6% PEG$_{4000}$: 0% |
| 26 | PC (50 nm) | OmpF crystal PEI | 1.35 | PEG$_{300}$: 13% PEG$_{600}$: 28% PEG$_{1100}$: 22% PEG$_{4000}$: 46% |
| 27 | PES (30 nm) | PAP[5] crystal MPD 0.25% TMC 0.0125% | 12.8 | PEG$_{300}$: 32% PEG$_{600}$: 36% PEG$_{1100}$: 33% PEG$_{4000}$: 34% |
| 28 | PC (50 nm) | PEI + PAP[5] crystal | To be tested | To be tested |
| 29 | PC (50 nm) | PEI + PAP[5] crystal | 1.1 | To be tested |

Table 2 shows the process details and remarks for each trial.

TABLE 2

| Trial | Process details | Remarks |
|---|---|---|
| 1 | MPD wetting: 10 minutes<br>Drying membrane surface<br>Interfacial reaction time with TMC: 1 minute | Brown stains appeared, we think the wet membrane cannot be dried. |
| 2 | MPD wetting: 10 minutes<br>Gently blotting excess MPD solution<br>Interfacial reaction time: 1 minute | Ununiformed TFC surface because of the residual water drop on the surface |
| 3 | MPD wetting: 10 minutes<br>Gently blotting excess MPD solution<br>Interfacial reaction time: 5 minute | Ununiformed TFC surface because of the residual water drop on the surface |
| 4 | MPD wetting: 10 minutes<br>Rubbing the membrane surface smoothly<br>Interfacial reaction time: 1 minute | Originally this membrane should be intact, but we damaged the membrane somehow. |
| 5 | Deposition of MPD and PAP[5] crystals: filtration (30 psi)<br>Drying membrane surface<br>Reaction time: 1 minute | Hexane has influence on the crystals. |
| 6 | Monomer deposition: filtration (60 psi)<br>Heated at 70° C. for 1 hour | |
| 7 | MPD wetting: 10 minutes<br>Rubbing the membrane surface smoothly<br>Interfacial reaction time with TMC: 1 minute | |
| 8 | MPD wetting: 10 minutes<br>Rubbing the membrane surface smoothly<br>Interfacial reaction time with TMC: 1 minute | Same rejection performance compared to commercial RO in dead end filtration cell |
| 9 | MPD wetting: 10 minutes<br>Rubbing the membrane surface smoothly<br>Interfacial reaction time with TMC: 1 minute | |
| 10 | Layer by layer PEI/PAP[5] crystals (2 layers)<br>MPD wetting: 10 minutes<br>Rubbing the membrane surface smoothly<br>Interfacial reaction time: 1 minute | We think PAP[5] crystals still cannot survive hexane. |
| 11 | PC membrane activated by UV/ozone for 30 s<br>Layer by layer PEI/OmpF crystals (1/5 button) (10 layers)<br>Filter with 1 mg/ml EDC and 1 mg/ml NHS at pH = 7<br>10 mM phosphate solution overnight | Tested in 10 ml cell |
| 12 | PC membrane activated by UV/ozone for 30 s<br>Layer by layer PEI/OmpF crystals (1/5 button) (6 layers)<br>Filter with 1 mg/ml EDC and 1 mg/ml NHS at pH = 7<br>10 mM phosphate solution overnight | Tested in 10 ml cell<br>Rejection of PEG600 was 93% in previous experiment |
| 13 | 79% (2000 ppm NaCl) | MPD wetting: 10 minutes<br>Rubbing the membrane surface smoothly<br>Interfacial reaction time with TMC: 1 minute |
| 14 | NA | MPD wetting: 10 minutes<br>Rubbing the membrane surface smoothly<br>Interfacial reaction time with TMC: 1 minute |
| 15 | 62% (2000 ppm NaCl) | MPD wetting: 10 minutes<br>Rubbing the membrane surface smoothly<br>Interfacial reaction time with TMC: 1 minute |
| 16 | $PEG_{300}$: ND<br>$PEG_{600}$: 0%<br>$PEG_{1100}$: 0%<br>$PEG_{4000}$: 4% | PES membrane activated by UV/ozone<br>Layer by layer PEI/PAP[5] crystals (1 button) (2 layers)<br>MPD filtration: 15 min<br>Interfacial reaction time with TMC: 1 minute |
| 17 | $PEG_{300}$: 4%<br>$PEG_{600}$: 2%<br>$PEG_{1100}$: 10%<br>$PEG_{4000}$: 9% | PC membrane activated by UV/ozone<br>Layer by layer PEI/PAP[5] crystals (1 button) (2 layers)<br>Filter with 1 mg/ml EDC, 1 mg/ml NHS and 0.1% MPD at pH = 7 solution overnight |
| 18 | $PEG_{300}$: 5%<br>$PEG_{600}$: 7%<br>$PEG_{1100}$: 10%<br>$PEG_{4000}$: 10% | PC membrane activated by UV/ozone<br>Layer by layer PEI/PAP[5] crystals (1 button) (3 layers)<br>Filter with 1 mg/ml EDC, 1 mg/ml NHS and 0.1% MPD at pH = 7 solution overnight |
| 19 | 87% (2000 ppm NaCl) | MPD wetting: Filtration with PAP[5] (2 buttons)<br>Rubbing the membrane surface smoothly<br>Interfacial reaction time with TMC: 1 minute |
| 20 | 90% (2000 ppm NaCl) | Post-MPD wetting after PAP[5] deposition (2 buttons)<br>Rubbing the membrane surface smoothly<br>Interfacial reaction time with TMC: 1 minute |
| 21 | ~100% (2000 ppm NaCl) | Same with #20 |
| 22 | ~80% (2000 ppm NaCl) | Same with #20 |
| 23 | ~0% (2000 ppm NaCl) | Same with #20s |
| 24 | $PEG_{300}$: ND<br>$PEG_{600}$: ND<br>$PEG_{1100}$: 53%<br>$PEG_{4000}$: 40% | Post-filtration of MPD after PAP[5] deposition (2 buttons)<br>Rubbing the membrane surface smoothly<br>Interfacial reaction time with TMC: 1 minute |

TABLE 2-continued

| Trial | Process details | Remarks |
|---|---|---|
| 25 | Repeat of #24 | Used wrong side of PES |
| 26 | Mix PEI with OmpF crystals (2 buttons) and filtration Layer by layer PEI/PAP[5] crystals (1/5 button) EDC/NHS filtration between and after every layer | Crystals quality is not good |
| 27 | Same with #20 | MPD solution disrupted/destroyed crystals |
| 28 | PC membrane activated by UV/ozone Layer by layer PEI/PAP[5] crystals (1 button) (2 layers) Filter with 1 mg/ml EDC and NHS at pH = 7 overnight | Used spacer |
| 29 | Same with #28 | |

Figure 11:
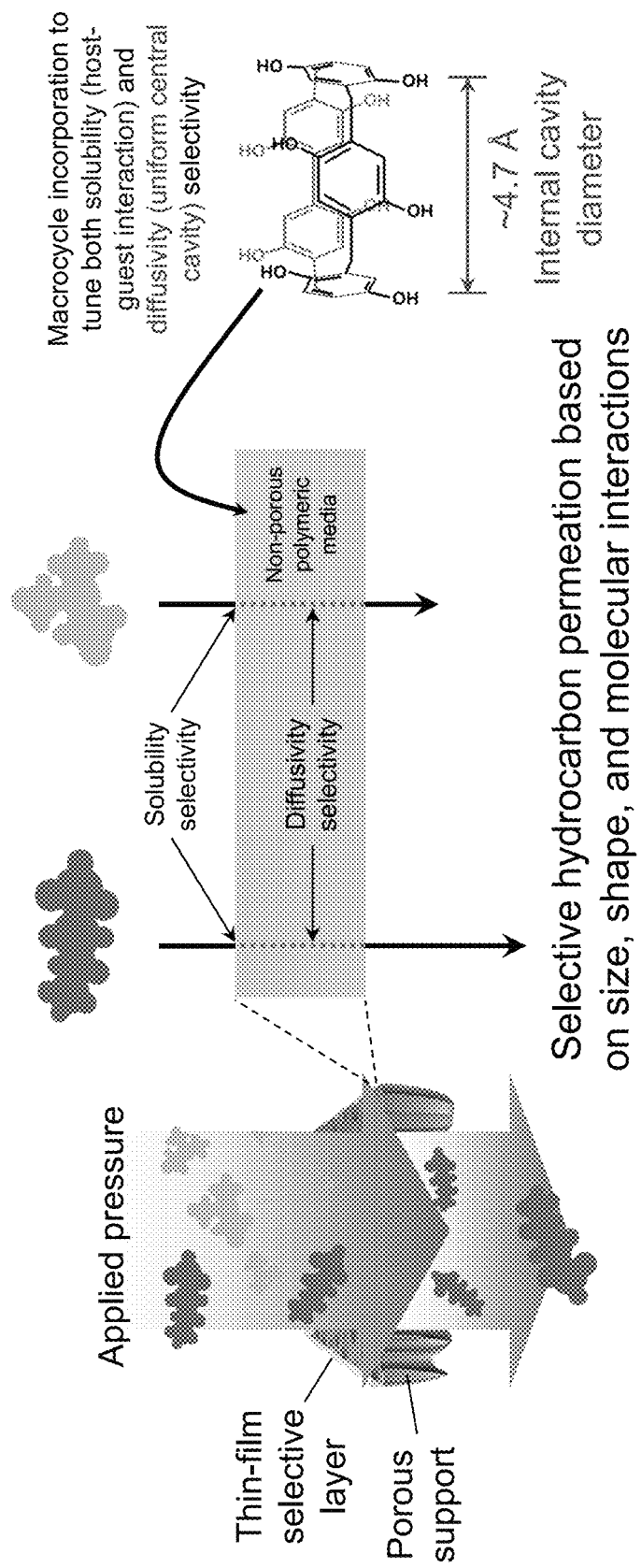
FIG. 11 depicts macrocycle incorporation into TFC membranes to tune permeability and selectivity for hydrocarbon separation.

Example 2. Macrocycle Incorporation into TFC Membranes to Tune Permeability and Selectivity for Hydrocarbon Separation The present invention comprises novel TFC membranes containing a small molecule pore element separated from a polymeric matrix element, enabling enhanced performance for gaseous, aqueous, organic solvent, and small molecule separation relative to leading membrane technologies. The present invention also relates to the incorporation of macrocycles into TFC membranes to tune both solubility (host-guest interaction) and diffusivity (uniform central cavity) selectivity (FIG. 11). The inventive TFC membranes demonstrate selective hydrocarbon permeation based on size, shape, and molecular interactions. Furthermore, there are several advantages of macrocycle-incorporated TFC membranes made by interfacial polymerization including that: (1) no additional infrastructure is required for industrial scale application and (2) the thin-selective layer formation which could lead to enhanced membrane productivity.

Figure 12:
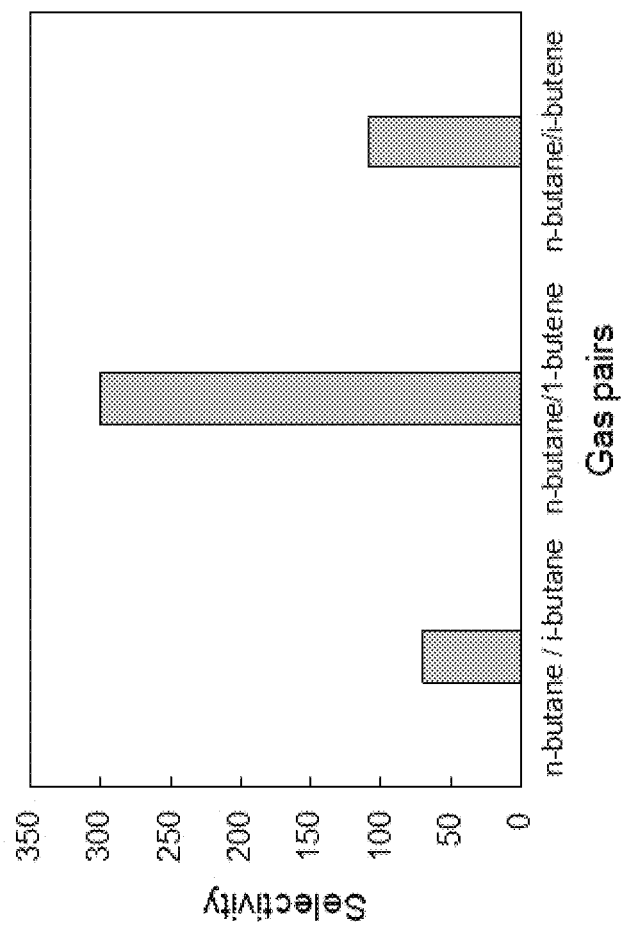
FIG. 12 depicts a preliminary hydrocarbon gas permeation test wherein $C_4$ separation was studied.
Figure 12:
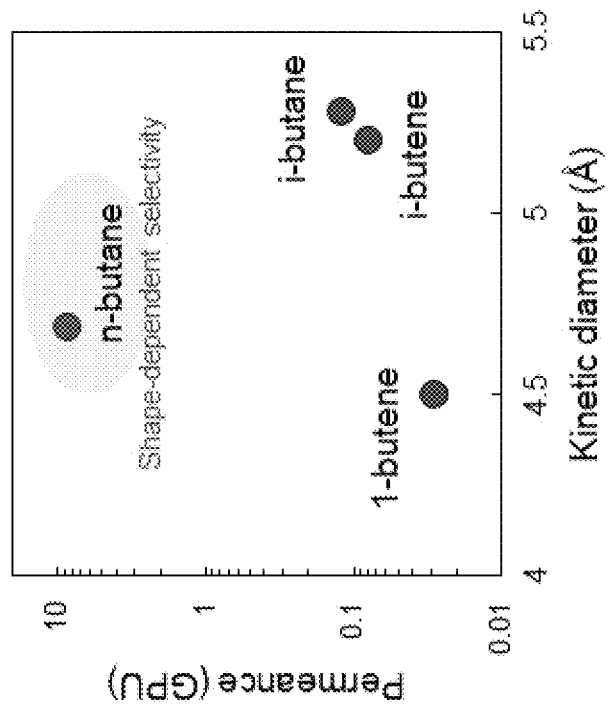
Figure 13:
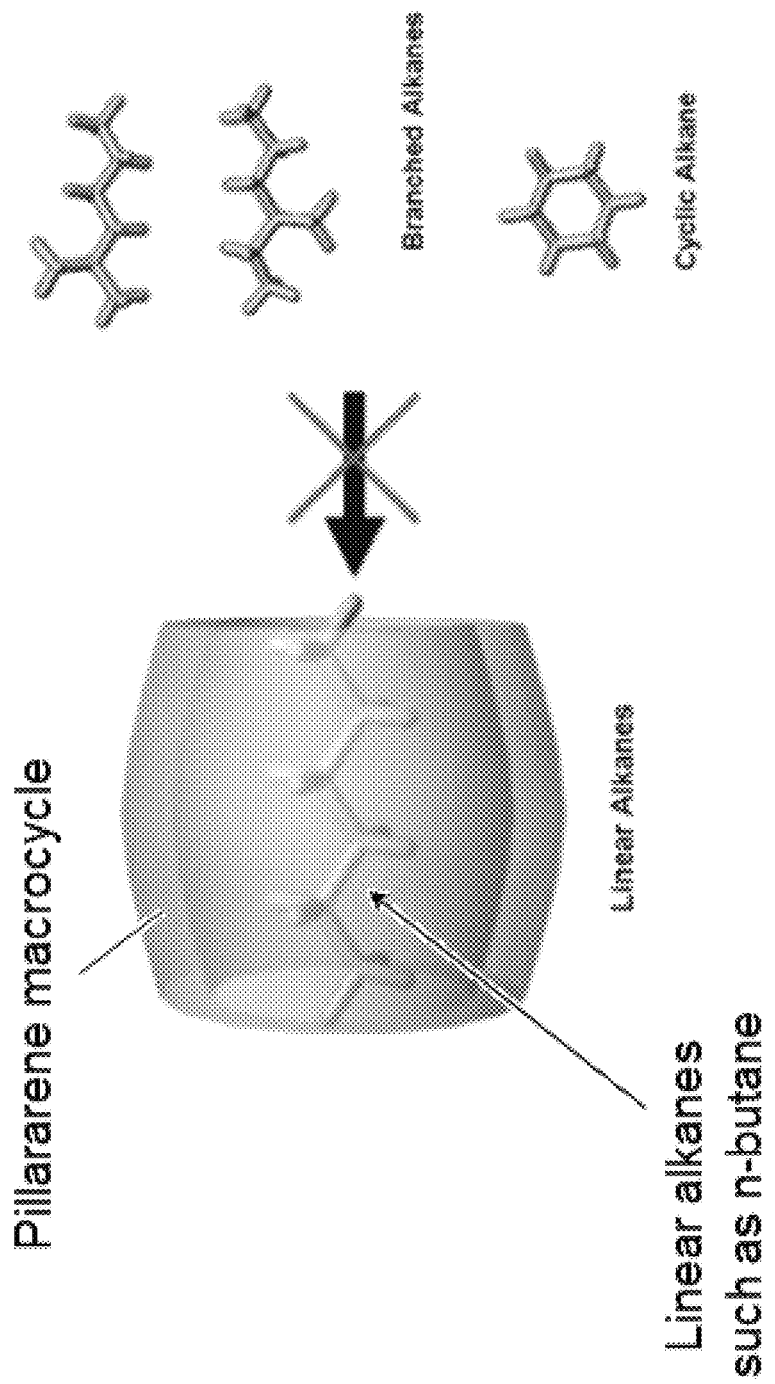
FIG. 13 depicts the outstanding selectivity of a pillararene macrocycle for n-butane.

The permeability and selectivity of the TFC membranes can be seen in the hydrocarbon gas permeation test wherein the separation of $C_4$ isomers was studied (FIG. 12). This test demonstrates that pillararene macrocycles of the present invention show outstanding selectivity for n-butane. The shape-dependent host-guest interaction between pillararene macrocycles and linear alkanes provides high selectivity of n-butane compared to other $C_4$ hydrocarbons (FIG. 13). The TFC membranes with incorporated macrocycles are also expected to have outstanding selectivity for $C_2$ (ethane/ethylene) and $C_3$ (propane/propylene) separations that are industrially impactful (Pillararenes, Tomoki Ogoshi, Ed., The Royal Society of Chemistry, 2016: pp. 1-315; Ogoshi et al., Angew. Chem. Int. Ed., 2018, 57:1592-1595; Ogoshi et al., J. Am. Chem. Soc. 2017, 139:5664-5667).

Figure 14:
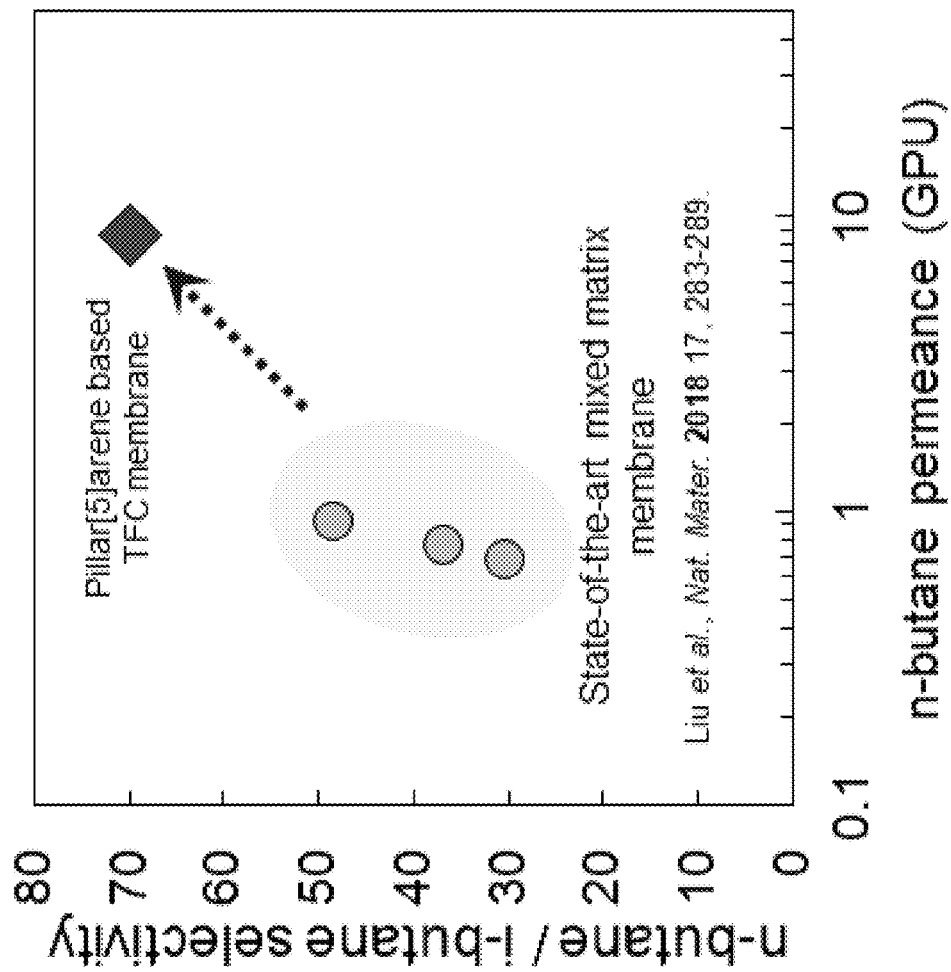
FIG. 14 depicts $C_4$ hydrocarbon separation using a pillar [5]arene based TFC membrane compared to state-of-the-art mixed matrix membranes.

A pillar[5]arene based TFC membrane was then compared to state-of-the-art $C_4$ hydrocarbon separation membranes (FIG. 14). The pillar[5]arene based TFC membrane demonstrated greater n-butane selectivity and permeance than the state-of-the-art membranes that were studied (Liu et al., Nat. Mater., 2018, 17:283-289).

The inventive TFC membranes with incorporated macrocycles have numerous financial benefits for use in industrial separations. For $C_2$ separation processes (ethane/ethylene), the hybrid membrane distillation system can reduce the costs of investigation and operations by ~67% and ~14%, respectively, compared to conventional distillation process (Benali et al., Sep. Purif. Technol., 2010, 73:377-390). For $C_3$ separation processes (propane/propylene), the operation cost can be reduced up to ~46% when the hybrid membrane-distillation is considered (Amedi et al., Ind. Eng. Chem. Res., 2018, 57:4366-4376). In addition, membrane development that exceeds current selectivity limit would be able to adopt entire membrane process that can reduce operation cost even further considered (Amedi et al., Ind. Eng. Chem. Res., 2018, 57:4366-4376). $C_4$ separation cost savings can be as high as 30% when membrane selectivity reaches up to 15 (Motelica et al., Ind. Eng. Chem. Res., 2012, 51:6977-6986). Preliminary membrane test result of macrocycle TFC membranes shows selectivity performance around ~70 to ~300, indicating impactful potential savings in industrial processes (compared to conventional distillation processes). It is not believed that any additional infrastructure is required for use of the inventive TFC membranes for industrial scale applications.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A thin film composite (TFC) membrane comprising a porous layer of at least one organic polymer, wherein the organic polymer further comprises macrocycles, wherein the macrocycle is a pillararene, a crown-ether, a calixarene, a porphyrin, or a combination thereof.

2. The TFC membrane of claim 1, wherein the macrocycle is selected from the group consisting of: pillar[4]arene, pillar[5]arene, pillar[6]arene, pillar[7]arene, pillar[8]arene, and combinations thereof.

3. The TFC membrane of claim 1, wherein the membrane further comprises a polymeric support.

4. The TFC membrane of claim 1, wherein the macrocycles comprise a pore having a diameter of 1 to 10 Å.

5. The TFC membrane of claim 1, wherein the membrane has a thickness between 1 nm and 1000 nm.

* * * * *